(12) United States Patent
Nan et al.

(10) Patent No.: US 8,470,763 B2
(45) Date of Patent: Jun. 25, 2013

(54) ALPHA-AMINO-N-SUBSTITUTED AMIDES, PHARMACEUTICAL COMPOSITION CONTAINING THEM AND USES THEREOF

(75) Inventors: Fajun Nan, Shanghai (CN); Jia Li, Shanghai (CN); Jian Ding, Shanghai (CN); Gang Liu, Shanghai (CN); Chuanming Xie, Shanghai (CN); Zehong Miao, Shanghai (CN); Wanyi Tai, Shanghai (CN)

(73) Assignee: Shanghai Institute of Materia Medica Chinese Academy of Sciences, Shanghai (CN)

( * ) Notice: Subject to any disclaimer, the term of this patent is extended or adjusted under 35 U.S.C. 154(b) by 304 days.

(21) Appl. No.: 12/747,485

(22) PCT Filed: Dec. 11, 2008

(86) PCT No.: PCT/CN2008/001996
§ 371 (c)(1),
(2), (4) Date: Sep. 7, 2010

(87) PCT Pub. No.: WO2009/074020
PCT Pub. Date: Jun. 18, 2009

(65) Prior Publication Data
US 2011/0021624 A1    Jan. 27, 2011

(30) Foreign Application Priority Data
Dec. 11, 2007   (CN) .......................... 2007 1 01720796

(51) Int. Cl.
*C07D 345/00* (2006.01)
(52) U.S. Cl.
USPC ............................................................ 514/1

(58) Field of Classification Search
USPC ............................................................ 540/1
See application file for complete search history.

(56) References Cited

FOREIGN PATENT DOCUMENTS
| | | |
|---|---|---|
| CN | 101092384 A | 12/2007 |
| WO | 2005/014574 A1 | 2/2005 |
| WO | 2006/056696 A2 | 6/2006 |

OTHER PUBLICATIONS

English Translation of Nan et al, CN 101092384 A, 2007.*
Bastin et al 'Salt Selection and Optimisation Procedures for Pharmacuetical New Chemical Entities' Organic Process Research and Development, vol. 4, p. 427-435, 2000.*

* cited by examiner

*Primary Examiner* — Brandon Fetterolf
*Assistant Examiner* — Christopher R Stone
(74) *Attorney, Agent, or Firm* — Baker & Hostetler LLP

(57) ABSTRACT

Disclosed are a series of α-amino-N-substituted amide compounds having a structure of the following formula, the pharmaceutically acceptable salts thereof, and the pharmaceutical composition comprising the same. The α-amino-N-substituted amide compounds or the pharmaceutically acceptable salts thereof according to the present invention have anti-tumor and/or anti-cancer activities in vivo and in vitro, can effectively depress the growth of various tumor cells and/or cancer cells, and thus can be used in preparing drugs for treating tumors and/or cancers.

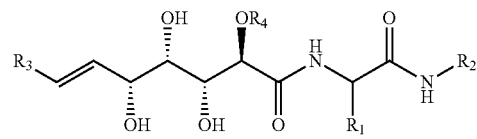

13 Claims, 1 Drawing Sheet

Inhibitory effects of L538 against human breast cancer cells MDA-MB-435 transplanted on nude mice Experimental therapeutic effects of L538 against human breast cancer cells MDA-MB-435 transplanted on nude mice

ALPHA-AMINO-N-SUBSTITUTED AMIDES, PHARMACEUTICAL COMPOSITION CONTAINING THEM AND USES THEREOF

CROSS-REFERENCE TO RELATED APPLICATIONS

This application is a National Stage of International patent application PCT/CN2008/001996, filed on Dec. 11, 2008, which claims priority to foreign patent application CN2007101720796, filed on Dec. 11, 2007.

TECHNICAL FIELD

The present invention relates to a series of α-amino-N-substituted amide compounds or the pharmaceutically acceptable salts thereof, the pharmaceutical composition comprising the same, and uses of the compounds and the pharmaceutically acceptable salts thereof in preparing anti-tumor and/or anti-cancer drugs.

BACKGROUND OF THE INVENTION

Cancer, which are a series of diseases characterized in abnormal cell proliferation and metastasis, has been one of the serious diseases that threaten the human health. According to the statistics from WTO, about 6 million peoples suffer newly from cancer every year all over the world. In China, cancer has been the second largest cause of death after cardiacerebral vascular diseases.

In the field of chemical treatment for tumor, effective drugs against various cancers have been studied for a long time. But unfortunately, although the developed anti-cancer drugs can kill cancer cells effectively, they are greatly toxic to normal cells. Patients taking those drugs showed weight loss, nausea, hallucinations, loss of appetite and other symptoms. In addition, the current chemotherapeutic agents can not provide ideal effects and broad-spectrums against tumors. Therefore, there is an urgent need for developing a chemotherapeutic agent, which can effectively treat various cancers with high selectivity and high efficiency.

Bengamides are a class of natural products from the ocean, which have significant antineoplasmic activities. Since the compounds were isolated from the marine sponge in 1986, their synthesis has been studied by a plural of research groups due to their extensive biological activities. Among them, bengamide B has the most prominent antineoplasmic activities, which shows activities against human tumor cells at a nanomolar level in all of the in vitro tests, and also can remarkably depress the growth of heterograft of MDA-MB-4355 human breast cancer cells in vivo. Since bengamide B has defects such as poor solubility, difficulties in synthesis, etc, Novartis performed a study on the synthesis of Bengamide analogues in 2001, and developed an analogue of the natural Bengamide B, LAF389, which has a good solubility, and activities in vitro and in vivo comparable to Bengamide B. Although LAF389 showed a good prospect in its initial stage, after it entered clinical study at 2001, it was found that the compound had side effects such as taste disturbance, blurred vision, etc., and did not possess the foreseen therapeutic effects, making no further development be performed.

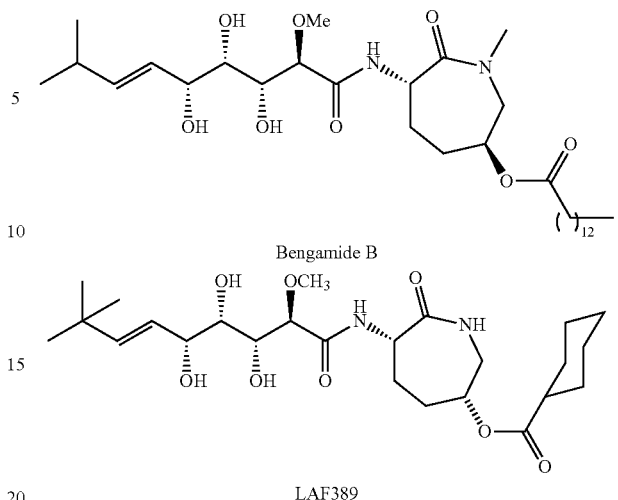

DISCLOSURE OF THE INVENTION

According to the present invention, a series of α-amino-N-substituted amide compounds which have a novel structure and anti-tumor and/or anti-cancer activities in vitro and in vivo, are synthesized by simplifying and modifying the structures of Bengamide B and LAF389.

Therefore, an object of the present invention is to provide a series of novel α-amino-N-substituted amide compounds or the pharmaceutically acceptable salts thereof, which can be used as an anti-tumor agent, so as to develop a route for searching for anti-tumor drugs or the lead compounds thereof.

Another object of the present invention is to provide a method for preparing the α-amino-N-substituted amide compounds.

Yet another object of the present invention is to provide pharmaceutical compositions comprising the above said α-amino-N-substituted amide compounds or the pharmaceutically acceptable salts thereof as an active component.

Still another object of the present invention is to provide uses of the above said α-amino-N-substituted amide compounds or the pharmaceutically acceptable salts thereof in preparing anti-tumor drugs.

The α-amino-N-substituted amide compound of the present invention has a structure represented by the following formula, wherein, $R_1$ is H or a substituted or unsubstituted C1-C10 alkyl, wherein the substituent of the substituted C1-C10 alkyl is selected from the group consisting of C1-C10 alkoxyl, C1-C10 alkylthio, hydroxyl, amino carbonyl, C1-C10 alkoxyl carbonyl, C1-C10 alkoxyl carbonyl amino, aryl, fused heteroaryl and (1-phenyl C1-4 alkoxylene methylene) imidazolyl;

R$_2$ is one selected from the group consisting of vinyl C1-C10 alkylene; hydroxyl C1-C10 alkylene; C3-C8 cycloalkyl amino carbonyl C1-C10 alkylene; C3-C8 cycloalkoxyl carbonyl C1-C10 alkylene; C1-C10 alkoxyl carbonyl C1-C10 alkylene; C1-C10 alkoxyl C1-C10 alkylene; C3-C8 cycloalkoxyl C1-C10 alkylene; phenyl C1-C4 alkoxylene C1-C10 alkylene; C3-C8 saturated or unsaturated cycloalkyl carbonyloxy C1-C10 alkylene; C3-C8 cycloalkyl carbonyl amino C1-C4 alkylene; C3-C8 cycloalkyl C1-C4 alkylene carbonyloxy C1-C10 alkylene; adamantyl carbonyloxy C1-C10 alkylene; phenyl carbonyloxy C1-C10 alkylene; furyl carbonyloxy C1-C10 alkylene; phenyl C1-C4 alkylene carbonyloxy C1-C10 alkylene; C1-C15 alkyl carbonyloxy C1-C10 alkylene; acetenyl C1-C10 alkylene carbonyloxy C1-C10 alkylene; C1-C15 alkoxyl carbonyloxy C1-C10 alkylene; C3-C 8 cycloalkoxyl carbonyloxy C1-C10 alkylene; phenyl C1-C10 alkoxylene carbonyloxy C1-C10 alkylene; azido C1-C15 alkylene carbonyloxy C1-C10 alkylene; alkylidyne of formula

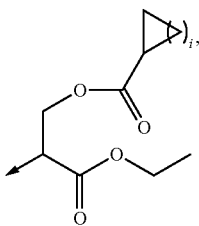

wherein, i is an integer of 1 to 6; spirolactone alkylene of formula

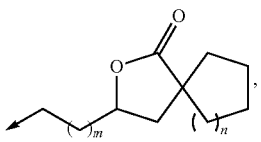

wherein, m is an integer of 0 to 5, and n is an integer of 0 to 4; and lactone methylene of formula

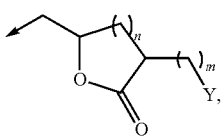

wherein, m is an integer of 0 to 5, n is an integer of 0 to 4, and Y is phenyl or a C1-C10 alkyl;

R$_3$ is a C1-C10 alkyl;

R$_4$ is a C1-C5 alkyl.

Herein, the terms used in the present invention are defined as follow. The alkyl includes linear or branched alkyl; the alkylene includes linear or branched alkylene. C1-C10 alkyl refers to a linear or branched alkyl containing 1 to 10 carbon atoms. C1-C10 alkylene refers to a linear or branched alkylene containing 1 to 10 carbon atoms. Also, in respect of terms such as C1-C4 alkyl, etc., a person skilled in the art can understand their meanings based on the above definitions. In addition, among the compounds of the present invention, all stereoisomers produced by substitution at the position of R$_1$ or R$_2$ may comprise the stereoisomers having the S or R configuration at the positions respectively, and other stereoisomers produced by introducing a chiral substituent. Thus, the compound of the present invention also includes all kinds of stereoisomers thereof.

In a preferred embodiment of the present invention:

R$_1$ is a substituted or unsubstituted C1-C4 alkyl, wherein the substituent of the substituted C1-C4 alkyl is selected from the group consisting of C1-C4 alkoxyl, C1-C4 alkylthio, hydroxyl, amino carbonyl, C1-C4 alkoxyl carbonyl, C1-C4 alkoxyl carbonyl amino, phenyl, indyl, benzofuryl, benzothienyl, N-methyl indyl or 1-benzyloxy-methylene imidazolyl. More specifically, the said R$_1$ is methyl, isopropyl, isobutyl, 2-methylpropyl or n-butyl, or is a C1-C4 alkyl substituted by tert-butoxy, methylthio group, 4-(1-benzyloxymethylene) imidazolyl, hydroxy, tert-butoxy carbonyl, amino carbonyl, 3-indyl, phenyl and tert-butoxy carbonyl amino;

R$_2$ is one selected from the group consisting of vinyl C1-C4 alkylene; hydroxyl C1-C4 alkylene; C3-C6 cycloalkyl amino carbonyl C1-C4 alkylene; C3-C6 cycloalkoxyl carbonyl C1-C4 alkylene; C1-C4 alkoxyl carbonyl C1-C4 alkylene; C1-C4 alkoxyl C1-C4 alkylene; C3-C6 cycloalkoxyl C1-C4 alkylene; phenyl C1-C4 alkoxylene C1-C4 alkylene; C3-C6 saturated or unsaturated cycloalkyl carbonyloxy C1-C4 alkylene; cyclohexyl carbonyl amino C1-C4 alkylene; C3-C6 cycloalkyl C1-C4 alkylene carbonyloxy C1-C4 alkylene; adamantyl carbonyloxy C1-C4 alkylene; phenyl carbonyloxy C1-C4 alkylene; furyl carbonyloxy C1-C4 alkylene; phenyl C1-C4 alkylene carbonyloxy C1-C4 alkylene; C1-C15 alkyl carbonyloxy C1-C4 alkylene; acetenyl C1-C10 alkylene carbonyloxy C1-C4 alkylene; C1-C15 alkoxyl carbonyloxy C1-C4 alkylene; C3-C8 cycloalkoxyl carbonyloxy C1-C4 alkylene; phenyl C1-C6 alkoxylene carbonyloxy C1-C4 alkylene; azido C1-C15 alkylene carbonyloxy C1-C4 alkylene; alkylidyne of formula

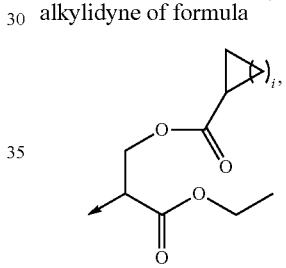

wherein, i is an integer of 1 to 4; spirolactone alkylene of formula

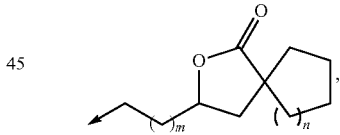

wherein, m is an integer of 0 to 3, and n is an integer of 0 to 2; and lactone methylene of formula

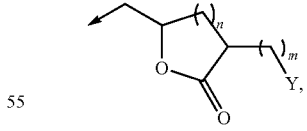

wherein, m is an integer of 0 to 3, n is an integer of 0 to 2, and Y is phenyl or a C1-C10 alkyl;

R$_3$ is a C1-C4 alkyl, and preferably tert-butyl or isopropyl;

R$_4$ is a C1-C4 alkyl, and preferably methyl or isopropyl.

In a more preferred embodiment:

R$_3$ is tert-butyl or isopropyl;

R$_4$ is methyl or isopropyl; and the combinations of R$_1$ and R$_2$ may be as follows, in the case of when R$_1$ is a substituted or unsubstituted C1-C4 alkyl, wherein the substituent of the substituted C1-C4 alkyl is selected from the group consisting of C1-C4 alkoxyl, C1-C4 alkylthio, hydroxyl, amino carbonyl, C1-C4 alkoxyl carbonyl and 1-benzyloxymethylene imidazolyl, $R_2$ is a vinyl C1-C4 alkylene; or in the case of when $R_1$ is a substituted or unsubstituted C1-C4 alkyl, wherein the substituent of the substituted C1-C4 alkyl is selected from the group consisting of 3-indyl and phenyl, $R_2$ is a hydroxyl C1-C4 alkylene; or in the case of when $R_1$ is a substituted or unsubstituted C1-C4 alkyl, wherein, the substituent of the substituted C1-C4 alkyl is C1-C4 alkoxyl carbonyl amino, $R_2$ is one selected from the group consisting of C3-C6 cycloalkyl amino carbonyl C1-C4 alkylene; C3-C6 cycloalkoxyl carbonyl C1-C4 alkylene; C1-C4 alkoxyl carbonyl C1-C4 alkylene; C1-C4 alkoxyl C1-C4 alkylene; C3-C6 cycloalkoxyl C1-C4 alkylene; phenyl C1-C4 alkoxylene C1-C4 alkylene; C3-C6 saturated or unsaturated cycloalkyl carbonyloxy C1-C4 alkylene; cyclohexyl carbonyl amino C1-C4 alkylene; C3-C6 cycloalkyl C1-C4 alkylene carbonyloxy C1-C4 alkylene; adamantyl carbonyloxy C1-C4 alkylene; phenyl carbonyloxy C1-C4 alkylene; furyl carbonyloxy C1-C4 alkylene; phenyl C1-C4 alkylene carbonyloxy C1-C4 alkylene; C1-C15 alkyl carbonyloxy C1-C4 alkylene; acetenyl C1-C10 alkylene carbonyloxy C1-C4 alkylene; C1-C15 alkoxyl carbonyloxy C1-C4 alkylene; C3-C8 cycloalkoxyl carbonyloxy C1-C4 alkylene; phenyl C1-C6 alkoxylene carbonyloxy C1-C4 alkylene; azido C1-C15 alkylene carbonyloxy C1-C4 alkylene; alkylidyne of formula

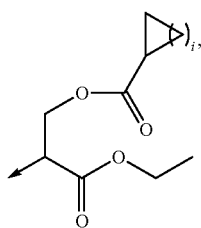

wherein, i is 3 or 4; spirolactone alkylene of formula

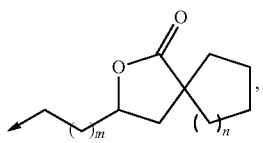

wherein, m is an integer of 0 to 3, and n is an integer of 0 to 2; and lactone methylene of formula

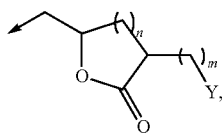

wherein, m is an integer of 0 to 3, n is an integer of 0 to 2, and Y is phenyl or a C1-C10 alkyl.

The α-amino-N-substituted amide compound of the present invention can be produced by following methods.

Method 1:

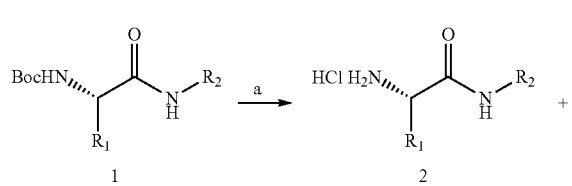

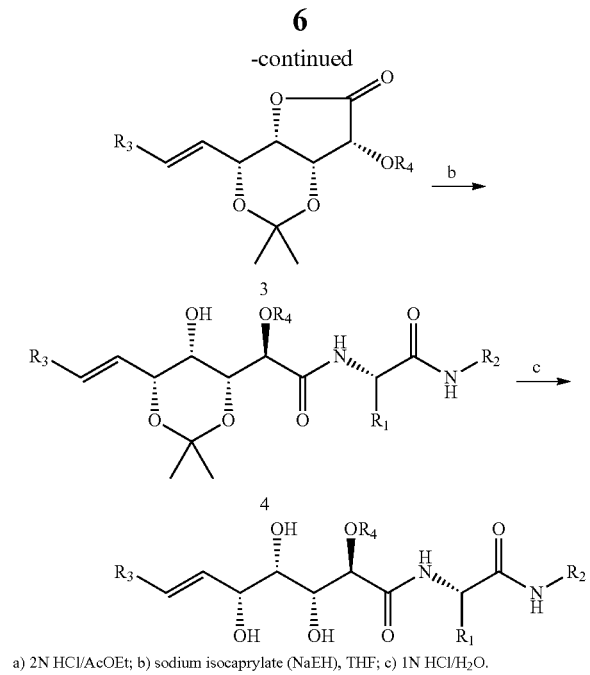

a) 2N HCl/AcOEt; b) sodium isocaprylate (NaEH), THF; c) 1N HCl/H₂O.

Wherein, $R_1$, $R_3$ and $R_4$ are defined as above; $R_2$ is one of all the other substituents except for the spirolactone alkylene of formula

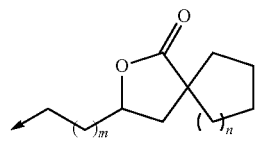

and the lactone methylene of formula

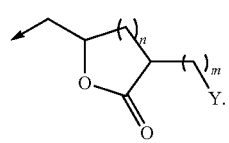

In an organic solvent, compound 1 is deprotected by removing the Boc (tert-butoxy carbonyl) protecting group in the presence of hydrochloric acid to give compound 2; then, compound 2 is coupled with compound 3 to afford compound 4 through lactone ring-opening reaction in the presence of NaEH; finally, compound 4 is converted to α-amino-N-substituted amide compound by the removal of a ketal under catalysis of an acid.

Method 2:

when $R_3$ is tert-butyl, $R_4$ and $R_1$ are each individually methyl, and $R_2$ is a lactone methylene selected from the group consisting of

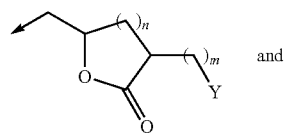 and

-continued

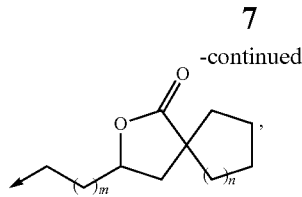

such α-amino-N-substituted amide compound e (R₂ is

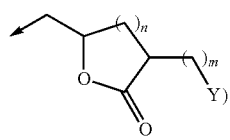

or f (R₂ is)

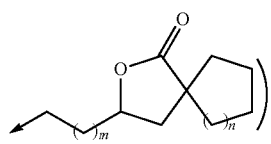

can be produced by the following method:

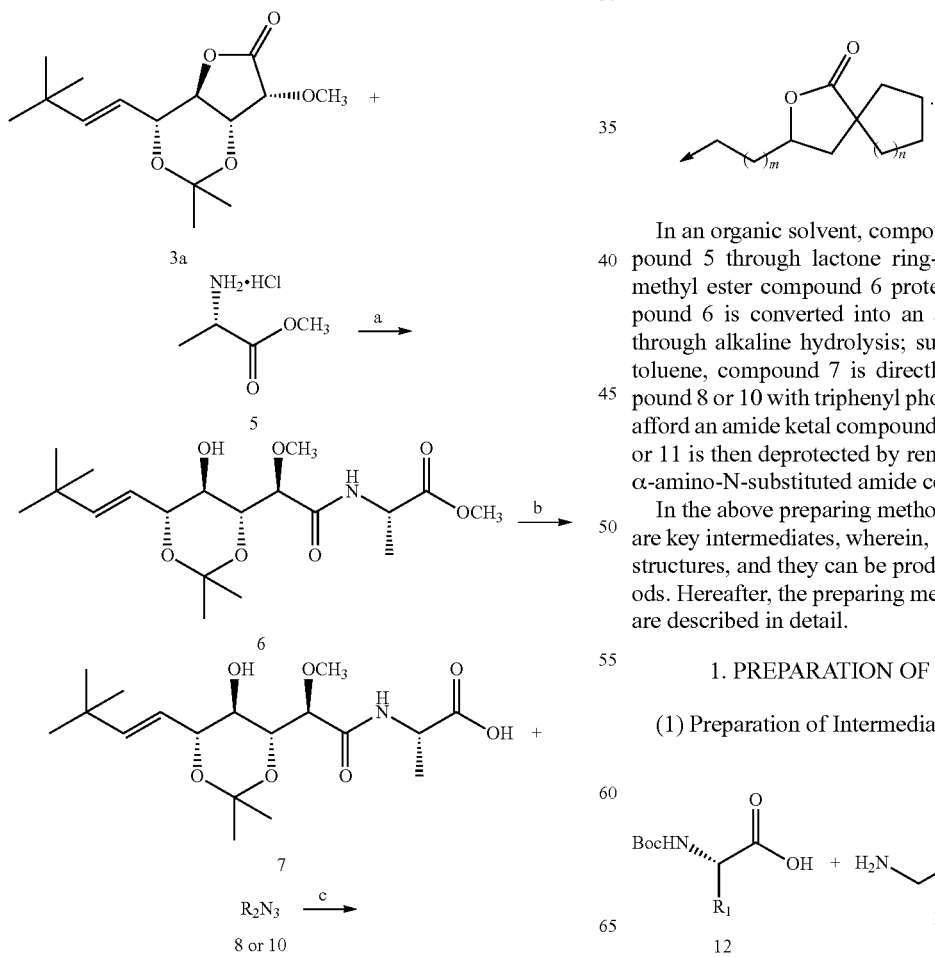

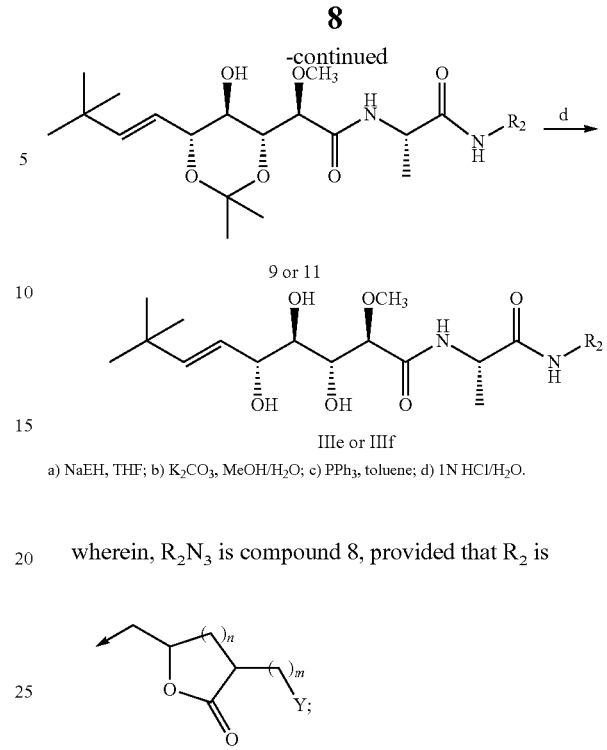

a) NaEH, THF; b) K₂CO₃, MeOH/H₂O; c) PPh₃, toluene; d) 1N HCl/H₂O.

wherein, $R_2N_3$ is compound 8, provided that $R_2$ is and $R_2N_3$ is compound 10, provided that $R_2$ is In an organic solvent, compound 3a is coupled with compound 5 through lactone ring-opening reaction to give a methyl ester compound 6 protected by a ketal; then, compound 6 is converted into an acid 7 protected by a ketal through alkaline hydrolysis; subsequently, in a solution of toluene, compound 7 is directly coupled with azido compound 8 or 10 with triphenyl phosphine as an intermedium to afford an amide ketal compound 9 or 11; finally, compound 9 or 11 is then deprotected by removing a ketal to provide the α-amino-N-substituted amide compound e or f.

In the above preparing methods, compound 1, 8, 10 and 3 are key intermediates, wherein, intermediate 1 has 7 types of structures, and they can be produced by the following methods. Hereafter, the preparing methods of those intermediates are described in detail.

1. PREPARATION OF INTERMEDIATE 1

(1) Preparation of Intermediate 1a:

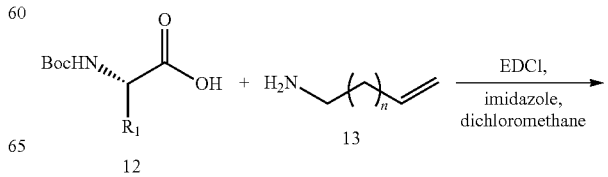

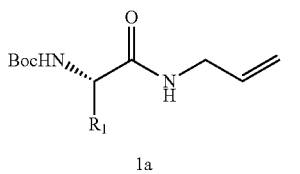

1a

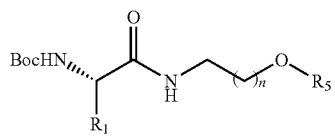

1c a) BiCl₃, triethyl silicane, acetonitrile; b) N₂H₄H₂O, ethanol; c) ditert-butyl dicarbonate ((Boc)₂O), NaHCO₃, AcOEt/H₂O; d) 2N HCl/AcOEt; e) 12, EDCI, imidazole, dichloromethane.

wherein, compound 12, compound 13, EDCI (N-ethyl-N'-(3-bimethylaminopropyl) carbodiimide hydrochloride) and imidazole are all commercially available products, and n is an integer of 1 to 4. After the above said compound 12 is dissolved in dichloromethane, compound 13 and imidazole are added thereinto, and intermediate 1a is obtained through EDCI condensation.

(2) Preparation of Intermediate 1b:

Wherein, $R_5$ is a C1-C4 alkyl, a C3-C6 cycloalkyl or a phenyl C1-C4 alkylene, and n is an integer of 0 to 3.

In an organic solvent, aldehyde or ketone 16' is reduced and esterified with a siloxane compound 15 protected by phthalimide to give compound 16; compound 16 is then deprotected with hydrazine hydrate, and its amino group is protected with ditert-butyl dicarbonate to afford ether compound 17 protected by Boc through column chromatography purification; finally, compound 17 is deprotected and reacted with compound 12 in the presence of a base and the condensating agent EDCI to provide the intermediate 1c.

(4) Preparation of Intermediate 1d:

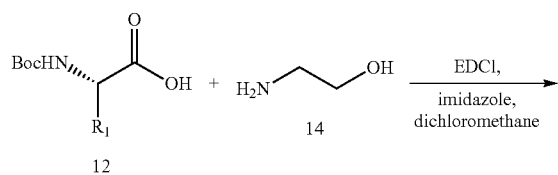

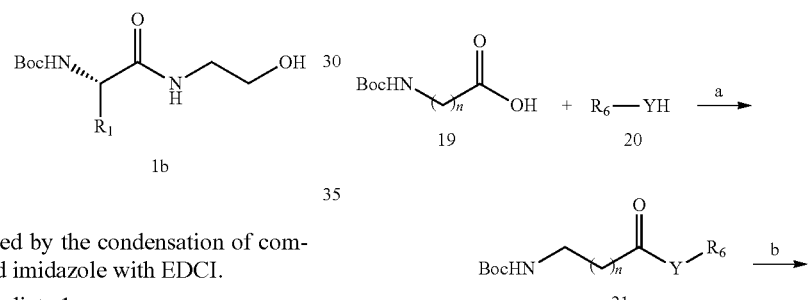

Intermediate 1b is obtained by the condensation of compound 12, compound 14 and imidazole with EDCI.

(3) Preparation of Intermediate 1c:

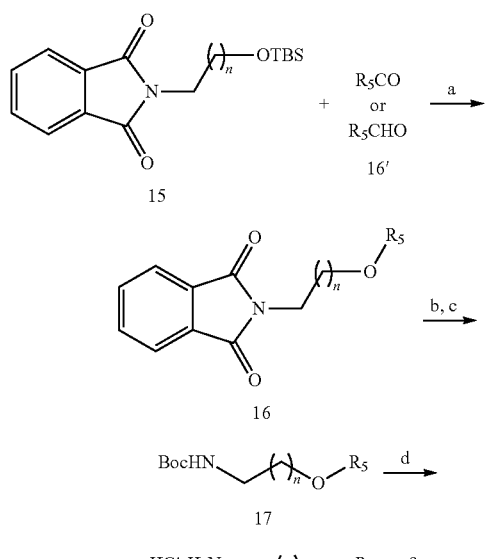

a) EDCI, imidazole, dichloromethane (DCM); b) 2N HCl/AcOEt; c) 12, EDCI, imidazole, DCM.

Wherein, Y is NH or O; $R_6$ is a C3-C6 cycloalkyl or a C1-C4 alkyl; n is an integer of 0 to 3.

In a solvent, the esterification or acylation between compound 19 and compound 20 is carried out to provide a coupled product 21; compound 21 is then deprotected by removing the Boc in the presence of hydrochloric acid to afford compound 22, the hydrochloride salt of compound 21; finally, compound 22 is acylated with compound 12 to provide the intermediate 1d.

(5) Preparation of intermediate 1e:

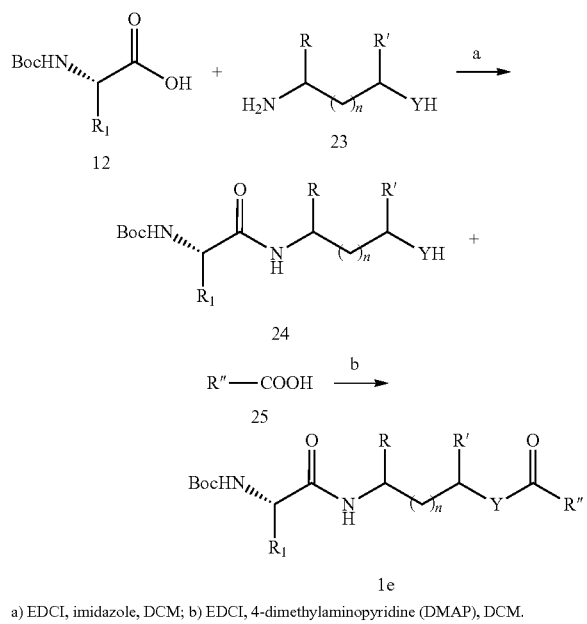

a) EDCI, imidazole, DCM; b) EDCI, 4-dimethylaminopyridine (DMAP), DCM.

Wherein, $R_1$ is a substituted or unsubstituted C1-C4 alkyl, wherein the substituents of the substituted C1-C4 alkyl are a C1-C4 alkoxyl carbonyl amino; n is an integer of 0 to 5; Y is NH or O; R and R' each individually is H or a C1-C4 alkyl; R" is one selected from the group consisting of C3-C6 saturated or unsaturated cycloalkyl, C3-C6 cycloalkyl C1-C4 alkylene, adamantyl, phenyl, furyl, phenyl C1-C4 alkylene, C1-C15 alkyl, acetenyl C1-C10 alkylene and azido C1-C15 alkylene.

In a solvent such as dichloromethane, in the present of a base such as imidazole, the amino acid 12 protected by Boc is amidated with an primary or secondary amine 23 to give compound 24; then, in a solvent such as dichloromethane, a catalyzing amount of a base such as DMAP (4-dimethyl amino pyridine), and a condensating agent EDCI are added thereinto, finally, compound 24 is acylated or esterified with substituted carboxylic acid 25 to provide the intermediate 1e.

(6) Preparation of Intermediate 1f:

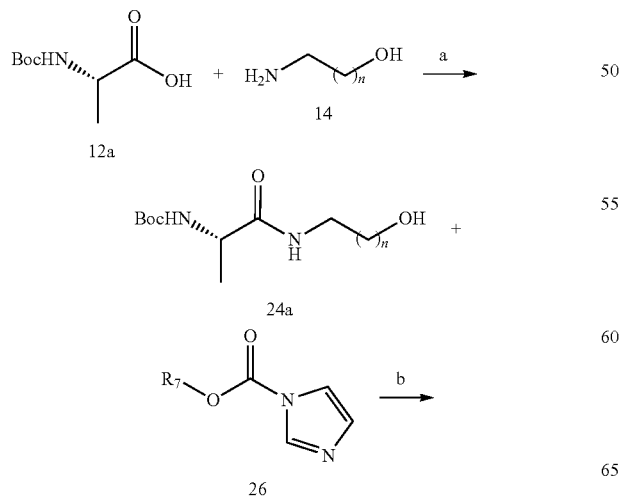

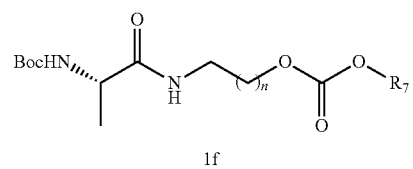

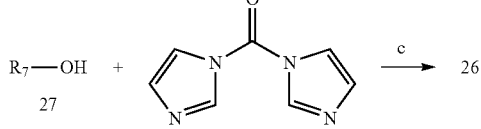

a) EDCI, imidazole, DCM; b) DBU (1,8-diazabicyclo[5.4.0]undec-7-ene), toluene; c) KOH, toluene.

Wherein, n is an integer of 1 to 3, and $R_7$ is one selected from the group consisting of C1-C15 alkyl, C3-C8 cycloalkyl and phenyl C1-C10 alkylene.

Compound 12a reacts with the amino group of amino-alcohol 14 through acylation to give compound 24a; then, in a toluene solution, in the presence of a base such as DBU (1,8-diazabicyclo[5.4.0]undec-7-ene), compound 24a is coupled with alcohol 26 activated by imidazolyl to afford the key intermediate 1f, wherein, compound 26 is obtained by reacting alcohol 27 with N,N'-carbonyldiimidazole in a toluene solution in the presence of a base such as KOH.

(7) Preparation of Intermediate 1g:

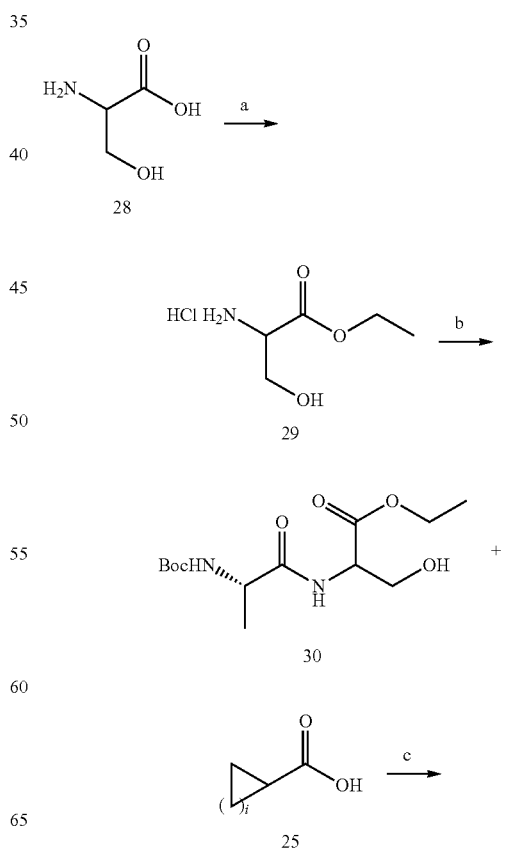

-continued

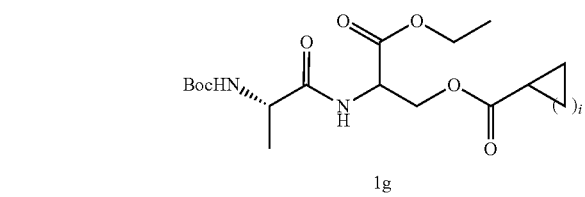

1g a) ethanol, SOCl₂; b) 12a, DCM, imidazole, EDCI; c) DCM, EDCI, 4-dimethylaminopyridine.

Wherein, i is an integer of 1 to 4.

In an ethanol solution of dichlorine sulfoxide, compound 28 is esterified to be converted into ethyl ester hydrochloride 29 thereof, which is then acylated with alanine 12a by using a condensating agent in the presence of a base in a solvent to give compound 30; then, in a dichloromethane solution, and in the present of a base and the condensating agent EDCI, compound 30 is esterified with cycloalkyl carboxylic acid 25 to provide the key intermediate 1g.

2. Preparation of Intermediate 8:

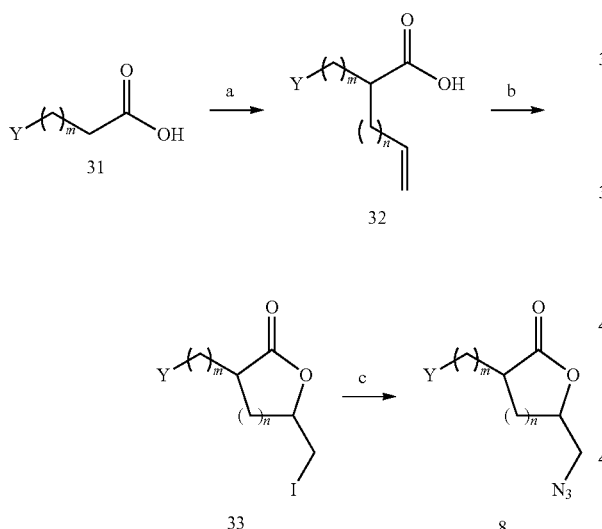

a) lithium diisopropylamide (LDA), tetrahydrofuran, [structure]; b) I₂, KI/H₂O, NaHCO₃, ethyl ether, c) NaN₃, N,N-dimethylformamide, 50.

Wherein, m is an integer of 0 to 5, n is an integer of 0 to 4, X is a halogen atom, and Y is phenyl or a C1-C10 alkyl.

In a tetrahydrofuran solution, the α-hydrogen of the alkyl carboxylic acid compound 31 substituted with Y was abstracted with a base such as lithium diisopropylamide, and then nucleophilically substituted with an alkenylalkyl compound at this position to provide compound 32; in the presence of a base, iodine and potassium iodide, compound 32 undergoes an iodolactonization in an ethyl ether solution to afford compound 33; subsequently, in a N,N-dimethylformamide solution, compound 33 is nucleophilically substituted by an azido compound to provide the key intermediate 8.

3. Preparation of Intermediate 10

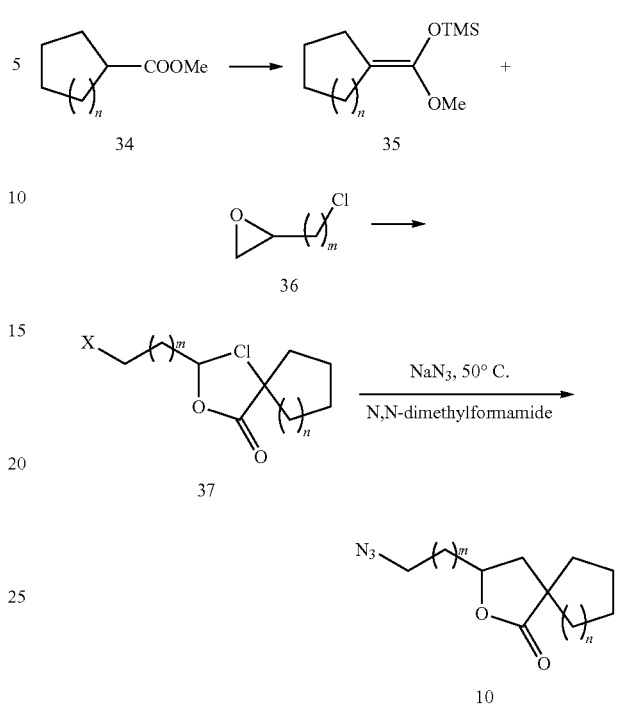

wherein, m is an integer of 0 to 5, and n is an integer of 0 to 4.

In a tetrahydrofuran solution, compound 34 is treated with a base such as lithium diisopropylamide, and then trimethylchlorosilane (TMSCl) is added thereinto to give a siloxane compound 35 having an ethylenic linkage. The compound 35 nucleophilically attacks the epoxy group of compound 36 to make it open and to be lactonized to afford compound 37 (the detailed reaction conditions are given in the references listed below), which is then nucleophilically attacked by an azido compound in a solvent such as N,N-dimethylformamide to provide the intermediate 10.

4. Preparation of Intermediate 3

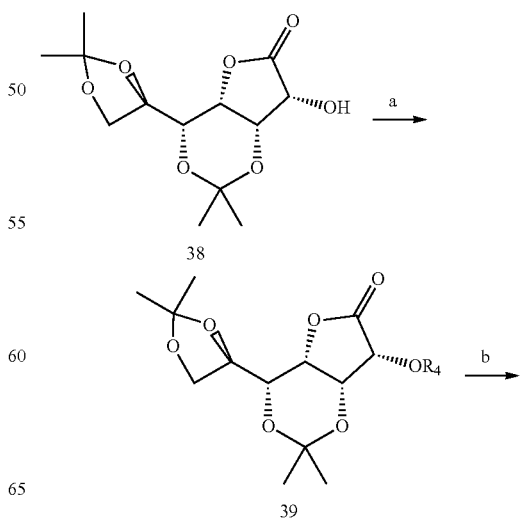

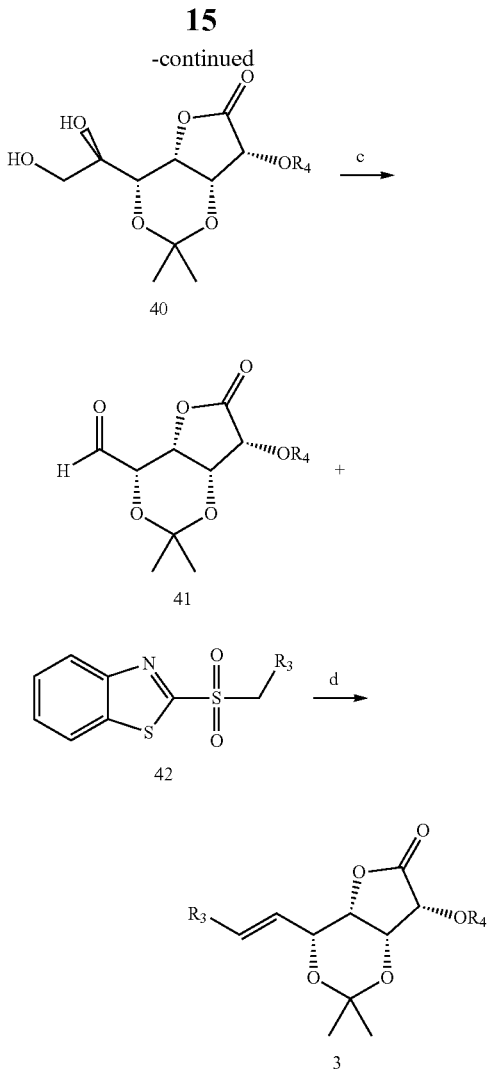

a) R₄I/Ag₂O, DCM; b) C₂H₅COOH/H₂O, p-toluene sulfonic acid; c) NaIO₄, acetonitrile/H₂O; d) n-butyllithium, tetrahydrofuran/acetonitrile, then trimethylchlorosilane and H₂O in turn.

Wherein, R3 is a C1-C10 alkyl; R4 is a C1-C5 alkyl.

In a solvent such as dichloromethane, compound 38 is alkylated with an alkyl iodide R₄I in the presence of silver chloride to give compound 39. Then in an aqueous propionic acid solution, is added a catalyzing amount of p-toluenesulfonic acid to selectively remove a ketal to afford compound 40, which is in turn oxidized by sodium periodate in an acetonitrile/H₂O solution to produce aldehyde 41. Subsequently, compound 41 is dissolved in a tetrahydrofuran/acetonitrile solution, and undergoes a Julia alkenylation to provide the intermediate 3.

For the preparing methods of some compounds in the present invention, reference is made to the following documents.

1. For the preparation of the compound 3 having a lactone side chain and the universal synthesis of compound 4 and, see *J. Med. Chem.*, 2001, 44, 3692-3699 and *Org. Process. Res. Dev.*, 2003, 7, 856-865;
2. For the synthesis of compound 15, see *J. Org. Chem.* 1982, 47, 2027-2033;
3. For the synthesis of compound 17, see *Tetrahedron Letters* 2002, 43, 6709-6713;
4. For the synthesis of compound 18, see *J. Med. Chem.* 1989, 32, 859-863;
5. For the synthesis of compound 37, see *Tetrahedron*, 2004, 60, 8957-8966;
6. For the synthesis of compound 42, see *Eur. J. Med. Chem. Chim. Ther.*, 1978, 13, 171;
7. For the synthesis of compound 25 wherein R″ is an azido C1-C15 alkylene, see *J. Am. Chem. Soc.* 2007, 129, 2744-2745.

In the present invention, the pharmaceutically acceptable salts of the compounds of formula can be additive salts of the present compounds with organic or inorganic acids, for example, those salts formed with hydrochloric acid, sulphuric acid, phosphoric acid, methanesulfonic acid, citric acid, fumaric acid, maleic acid, benzoic acid, benzenesulfonic acid, succinic acid, tartaric acid, lactic acid or acetic acid, preferably those salts formed with hydrochloric acid or methanesulfonic acid. For instance, curtain compounds of formula I in the form of free base can be reacted with hydrochloric acid to generate the corresponding salts in the form of hydrochloride, and with methanesulfonic acid to produce the corresponding salts in the form of methanesulfonate.

The present invention provides a pharmaceutical anti-tumor and/or anti-cancer composition comprising one or more selected from the above said α-amino-N-substituted amide compounds or the pharmaceutically acceptable salts thereof of the present invention as an active component, which may further comprises conventional pharmaceutical adjuvants, such as an excipient, a disintegrating agent, an antioxidant, a sweeting agent, a coating agent and so on.

The α-amino-N-substituted amide compounds or the pharmaceutically acceptable salts thereof provided by the present invention can be used to prepare drugs against tumor and/or cancer, such as gastric cancer, ovarian cancer, prostatic cancer, liver cancer, breast cancer, colon cancer, lung cancer or uterine cervix cancer.

The anti-tumor compounds provided by the present invention are prepared by a simple method, and can be effectively used to against tumor cells and/or cancer cells, thus having a good prospect in developing drugs.

DETAILED DESCRIPTION

Figure 1:
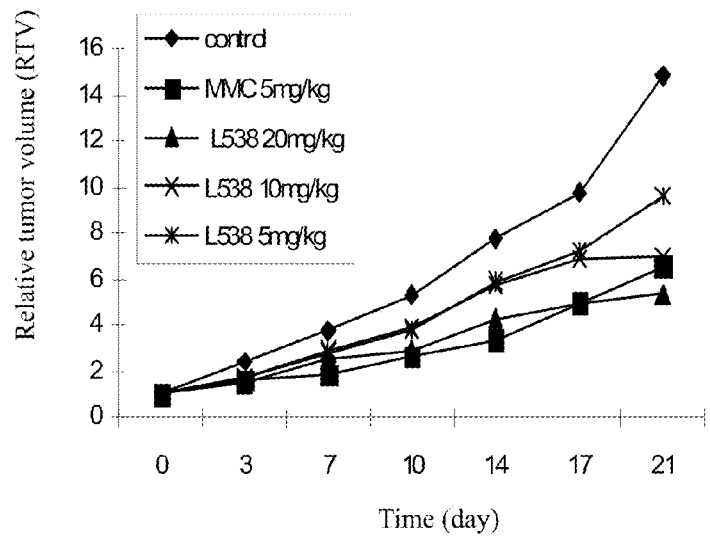
FIG. 1 is a graph illustrating the growth inhibiting effects of the active compound L538 on the MDA-MB-435 transplanted tumor, which is developed by subcutaneously inoculating human breast cancer MDA-MB-435 cell line on nude mice.

Best Mode for Carry Out the Invention

The present invention will be further described with reference to the following examples, but the invention is not limited thereto.

In the following examples, NMR spectra was determined on a MerCury-Vx 300M instrument manufactured by Varian (NMR calibration: δH 7.26 ppm (CDCl₃)). The reagents used in this invention were mainly provided by Shanghai Chemical Reagents Company, and the products were mainly purified through column chromatography with a crude-pored silica gel (mesh 200-300, model ZLX-) produced by Branch of Qingdao Haiyang Chemical Plant.

The conventional post-treatments used in the following reactions were as follows.

After the reaction was accomplished, an appropriate amount of solvent was added into to dilute the reaction mixture. Then the mixture was transferred to a separating funnel, and washed with water. The aqueous phase was extracted with the organic solvent again, and the organic phases were combined. If necessary, the reaction mixture was washed with a 5% HCl solution and/or a saturated NaHCO₃ solution, water and saturated saline in turn. After that, the organic phase was dried over anhydrous Na₂SO₄ or anhydrous MgSO₄, filtered and concentrated to provide a crude product, which was then purified through column chromatography to afford the final product.

PREPARATION EXAMPLE 1

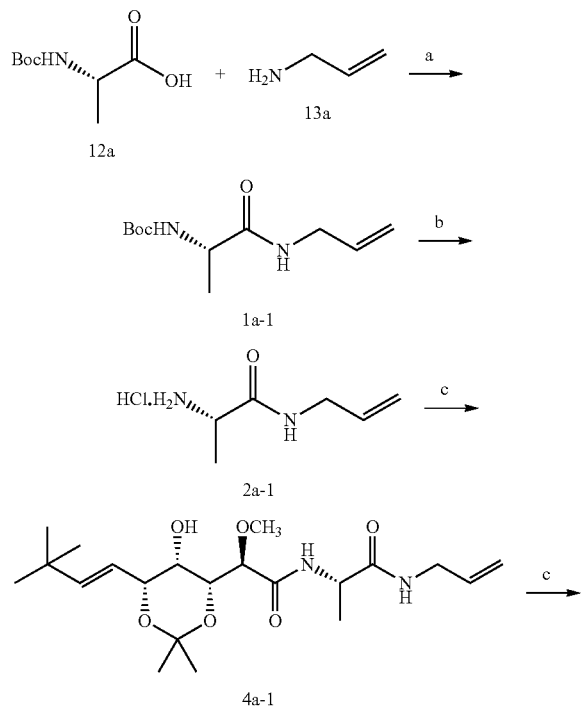

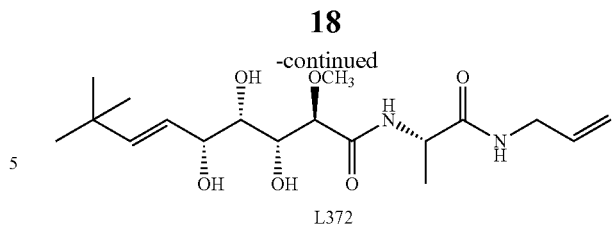

a) EDCI, imidazole, DCM; b) 2 N HCl/AcOEt; c) 3a, sodium isocaprylate, tetrahydrofuran; d) 1 N HCl/H₂O To a solution of compound 12a (2 mmol) in 15 ml of dry dichloromethane, were added subsequently compound 13a (4 mmol), EDCI (3 mmol) and imidazole (3 mmol). After agitated for 12 h at room temperature, the reaction mixture was diluted with 50 ml of dichloromethane, washed with water and then with saturated saline, dried and concentrated. Then, the resultant residue was separated through column chromatography eluting with petroleum ether/ethyl acetate (volume ratio: about 3:1) to afford compound 1a-1 (1.2 mmol).

Compound 1a-1 was inputted into a 10 ml single-necked flask, and 3 ml of 2N HCl/AcOEt was added thereinto. After stirred at room temperature for 1.5 h, the reaction mixture was concentrated through rotary evaporation to dryness to remove the solvent, and thereby afford compound 2a-1 (1.2 mmol).

After that, compound 2a-1 was inputted in a 10 ml single-necked flask, and 3 ml tetrahydrofuran and sodium isocaprylate (4 mmol) were added thereinto under stirring, followed by the addition of compound 3a (1.2 mmol). After stirred at room temperature for 16 h, the reaction mixture was concentrated through rotary evaporation to remove the solvent. The resultant residue was transferred with AcOEt, extracted, washed with water and then with saturated saline, died and concentrated. The residue was separated through column chromatography eluting with chloroform/methanol (volume ratio: about 50:1) to give compound 4a-1.

To a solution of compound 4a-1 in a 10 ml single-necked flask, were added 1.5 ml of tetrahydrofuran and 1.5 ml of hydrochloric acid (1N) at room temperature. After stirred for 1 h at room temperature, the reaction mixture was neutralized with a few drops of aqueous ammonia under ice bath, and rotarily evaporated to dryness to remove all the solvent. The resultant residue was separated by column chromatography eluting with chloroform/methanol (volume ratio: about 50:2) to provide the target compound L372.

The target compounds in the following table 1 were produced with the same method as that in Preparation Example 1, expect various substituted amino acids (compound 12) instead of the alanine 12a protected by Boc, and various compound 13 instead of the compound 13a, listed in the following Table 1:

TABLE 1

| No. | Compound 12 | Compound 13 | Target Compound |
|---|---|---|---|
| L372 | BocHN-CH(CH₃)-COOH | H₂N-CH₂-CH=CH₂ | (structure shown) |

¹H NMR (CDCl₃, 300 MHz) δ 1.03 (s, 9H), 1.45 (d, 3H), 3.51 (s, 3H), 3.65 (s, 1H), 3.90~3.79 (m, 4H), 3.95 (d, 1H), 4.21 (t, 1H), 4.51 (m, 1H), 5.22~5.10 (t, 2H), 5.45 (dd, 1H), 5.80 (m, 1H), 5.82 (d, 1H), 6.83 (m, 1H), 7.25 (d, 1H)

TABLE 1-continued

| No. | Compound 12 | Compound 13 | Target Compound |
|---|---|---|---|
| L444i | BocHN-Ser(OtBu)-OH | H₂N-allyl | (structure) |

¹H NMR (CDCl₃, 300 MHz) δ 1.03 (s, 9H), 1.20 (s, 9H), 3.45 (m, 1H), 3.51 (s, 3H), 3.65 (s, 1H), 3.81 (d, 1H), 4.00~3.85 (m, 7H), 4.21 (t, 1H), 4.51 (m, 1H), 5.22~5.10 (t, 2H), 5.45 (dd, 1H), 5.80 (m, 1H), 5.82 (d, 1H), 6.95 (m, 1H), 7.60 (d, 1H)

| L432 | BocHN-Met-OH | H₂N-allyl | (structure) |

¹H NMR (CDCl₃, 300 MHz) δ 1.03 (s, 9H), 2.07 (s, 3H), 2.30~2.00 (m, 1H), 2.60 (t, 2H), 3.51 (s, 3H), 3.65 (s, 1H), 3.90~3.79 (m, 4H), 3.95 (d, 1H), 4.21 (t, 1H), 4.61 (m, 1H), 5.22~5.10 (t, 2H), 5.45 (dd, 1H), 5.80 (m, 1H), 5.82 (d, 2H), 6.79 (m, 1H), 7.50 (d, 1H)

| L558b | BocHN-His(CH₂OBn)-OH | H₂N-allyl | (structure) |

¹H NMR (CDCl₃, 300 MHz) δ 1.03 (s, 9H), 3.19 (t, 2H), 3.51 (s, 3H), 3.61 (s, 1H), 3.90~3.79 (m, 4H), 3.95 (d, 1H), 4.21 (t, 1H), 4.85 (m, 1H), 5.10~5.00 (t, 2H), 5.35 (d, 2H), 5.45 (dd, 1H), 5.63 (m, 1H), 5.80 (d, 1H), 6.60 (m, 1H), 6.95 (s, 1H), 7.40-7.25 (m, 8H), 7.50 (s, 1H)

| L388 | BocHN-Ser-OH | H₂N-allyl | (structure) |

¹H NMR (CDCl₃, 300 MHz) δ 1.03 (s, 9H), 3.51 (s, 3H), 3.65 (s, 1H), 3.82 (m, 4H), 3.95 (m, 1H), 4.21 (m, 1H), 4.55 (m, 1H), 5.22~5.10 (t, 2H), 5.45 (dd, 1H), 5.80 (m, 1H), 5.82 (d, 1H), 7.10 (m, 1H), 7.70 (d, 1H)

TABLE 1-continued

| No. | Compound 12 | Compound 13 | Target Compound |
|---|---|---|---|
| L486e | | | |

¹H NMR (CDCl₃, 300 MHz) δ 1.03 (s, 9H), 1.45 (s, 9H), 2.30~1.90 (m, 2H), 2.60~2.30 (m, 2H), 3.51 (s, 3H), 3.63 (d, 1H), 3.80 (d, 1H), 3.85 (m, 4H), 3.95 (d, 1H), 3.15 (m, 1H), 4.21 (t, 1H), 4.47 (m, 1H), 5.19~5.10 (t, 2H), 5.45 (dd, 1H), 5.80 (m, 1H), 5.82 (d, 1H), 6.80 (m, 1H), 7.65 (d, 1H)

| L415 | | | |

¹H NMR (CDCl₃, 300 MHz) δ 1.03 (s, 9H), 3.02 (d, 2H), 3.51 (s, 3H), 3.68 (s, 1H), 3.90~3.79 (m, 6H), 3.98 (s, 1H), 4.21 (t, 1H), 4.91 (m, 1H), 5.22~5.10 (t, 2H), 5.45 (dd, 1H), 5.80 (m, 1H), 5.82 (d, 1H), 7.21 (m, 1H), 7.58 (d, 1H)

| L400 | | | |

¹H NMR (CDCl₃, 300 MHz) δ 0.95 (d, 6H), 1.03 (s, 9H), 2.39 (m, 1H), 3.51 (s, 3H), 3.65 (s, 1H), 3.90~3.79 (m, 5H), 3.98 (d, 1H), 4.15 (m, 1H), 4.25 (t, 1H), 4.29 (m, 1H), 5.22~5.10 (t, 2H), 5.45 (dd, 1H), 5.80 (m, 1H), 5.82 (d, 1H), 6.50 (m, 1H), 7.21 (d, 1H)

| L376 | | | |

¹H NMR (CDCl₃, 300 MHz) δ 1.03 (s, 9H), 1.45 (d, 3H), 3.51 (s, 3H), 3.52 (m, 3H), 3.70~3.65 (m, 4H), 3.80 (d, 1H), 4.01 (s, 1H), 4.20 (m, 2H), 4.51 (m, 2H), 5.45 (dd, 1H), 5.82 (d, 1H), 7.28 (m, 1H), 7.45 (d, 1H)

| L491 | | | |

¹H NMR (CDCl₃, 300 MHz) δ 1.03 (s, 9H), 1.65 (m, 2H), 3.05 (m, 1H), 3.15 (s, 3H), 3.40 (m, 3H), 3.45 (m, 3H), 3.65 (d, 2H), 3.95 (d, 1H), 4.15 (m, 1H), 4.25 (m, 1H), 4.80 (m, 1H), 5.42 (dd, 1H), 5.80 (d, 1H), 7.25~7.05 (m, 3H), 7.40 (d, 1H), 7.62 (d, 1H), 8.25 (m, 1H)

TABLE 1-continued

| No. | Compound 12 | Compound 13 | Target Compound |
|---|---|---|---|
| L418b | BocHN-Leu-OH | H₂N-CH₂CH₂-OH | (target structure with Leu-NHCH₂CH₂OH) |

¹H NMR (CDCl₃, 300 MHz) δ 0.95 (d, 6H), 1.03 (s, 9H), 1.90~1.50 (m, 3H), 3.02 (m, 1H), 3.51 (s, 3H), 3.52 (m, 3H), 3.65 (m, 1H), 3.78 (d, 1H), 3.82 (d, 1H), 4.01 (s, 1H), 4.10 (m, 1H), 4.18 (m, 2H), 4.22 (m, 2H), 4.45 (m, 2H), 5.45 (dd, 1H), 5.82 (d, 1H), 6.82 (m, 1H), 7.05 (d, 1H)

| No. | Compound 12 | Compound 13 | Target Compound |
|---|---|---|---|
| L452 | BocHN-Phe-OH | H₂N-CH₂CH₂-OH | (target structure with Phe-NHCH₂CH₂OH) |

¹H NMR (CDCl₃, 300 MHz) δ 1.03 (s, 9H), 1.35 (m, 2H), 3.05 (m, 1H), 3.11 (s, 3H), 3.20 (m, 1H), 3.35 (m, 1H), 3.50 (m, 2H), 3.60 (m, 2H), 3.65 (m, 2H), 3.95 (s, 1H), 4.18 (m, 2H), 4.75 (m, 1H), 5.42 (dd, 1H), 5.80 (d, 1H), 7.18 (d, 1H), 7.32~7.20 (m, 5H), 7.38 (m, 1H)

PREPARATION EXAMPLE 2

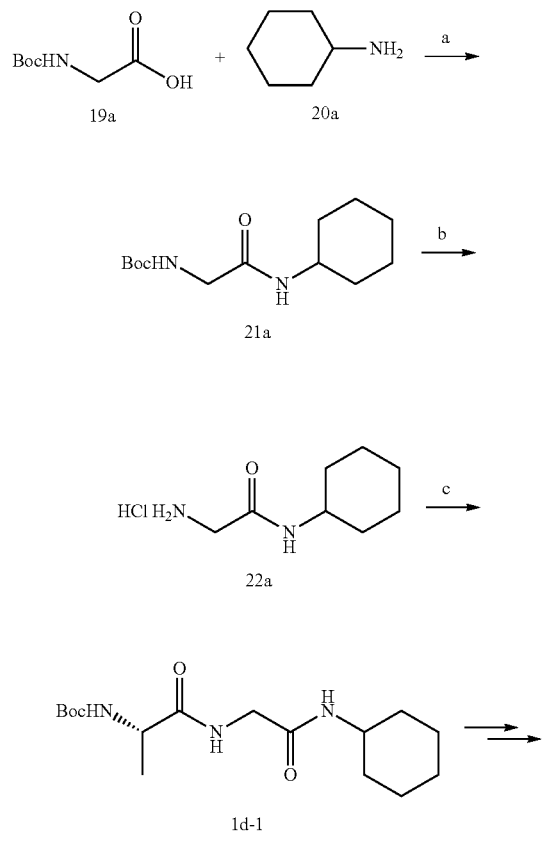

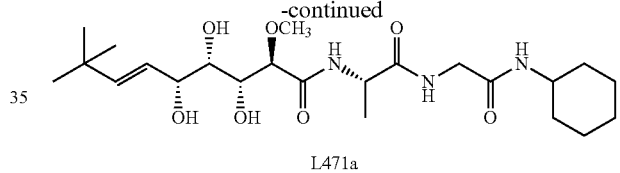

L471a a) EDCI, imidazole, DCM; b) 2 N HCl/AcOEt; c) 12a, EDCI, imidazole, DCM。

To a solution of compound 19a (2 mmol) in 10 ml of dry dichloromethane, were subsequently added thereinto compound 20a (4 mmol), EDCI (3.5 mmol) and imidazole (3.5 mmol). After stirred for 15 h at room temperature, the reaction mixture was diluted with 50 ml of dichloromethane, washed with water and then saline, dried and concentrated. The resultant residue was separated by column chromatography eluting with petroleum ether/ethyl acetate (volume ratio: about 5:1) to afford compound 21a.

Compound 21a was dissolved in 3 ml of 2N HCl/AcOEt solution, and stirred for 1.5 h at room temperature. The finish of the reaction was tracked and monitored by TLC. After that, the reaction mixture was rotarily evaporated to dryness to give compound 22a.

To a solution of 22a (1 mmol) in 4 ml of dry DCM, were added thereinto imidazole (1.5 mmol), EDCI (1.5 mmol) and compound 12a (1.5 mmol). After stirred for 15 h at room temperature, the reaction mixture was diluted with 50 ml of dichloromethane, washed with water and then with saline, died and concentrated. The resultant residue was separated by column chromatography eluting with petroleum ether/ethyl acetate (volume ratio: about 3:1) to afford compound 1d-1.

The compound 1d-1 was treated according to the subsequent processes in Example 1 to provide compound L471.

The target compounds in the following table 2 were produced with the same method as that in Preparation Example 2, expect various compound 20 listed in table 2 instead of the compound 20a:

TABLE 2

| No. | Compound 20 | Target Compound |
|---|---|---|
| L471 | cyclohexyl-NH₂ | (structure shown) |

¹H NMR (CDCl₃, 300 MHz) δ 1.03 (s, 9H), 1.45 (d, 3H), 1.90~1.20 (m, 10H), 3.01 (s, 1H), 3.51 (s, 3H), 3.65 (t, 2H), 3.90~3.79 (m, 5H), 4.01 (m, 1H), 4.15 (t, 1H), 4.25 (m, 1H), 5.45 (dd, 1H), 5.85 (d, 1H), 6.20 (d, 1H), 7.43 (m, 1H)

| L472-4 | cyclohexyl-OH | (structure shown) |

¹H NMR (CDCl₃, 300 MHz) δ 1.03 (s, 9H), 1.45 (d, 3H), 1.90~1.20 (m, 10H), 3.05 (s, 1H), 3.51 (s, 3H), 3.65 (s, 2H), 3.90 (d, 1H), 4.00~3.90 (m, 4H), 4.03 (m, 1H), 4.21 (br, 1H), 4.60 (m, 1H), 4.80 (m, 1H), 5.45 (dd, 1H), 5.85 (d, 1H), 7.01 (m, 1H), 7.20 (d, 1H)

| L418 | ethanol | (structure shown) |

¹H NMR (CDCl₃, 300 MHz) δ 1.03 (,s 9H), 1.30 (t, 3H), 1.45 (d, 2H), 3.29 (s, 1H), 3.50 (s, 3H), 3.65 (s, 1H), 3.93 (m, 3H), 3.95 (m, 1H), 4.00 (q, 2H), 4.25~4.15 (m, 3H), 4.60 (m, 1H), 5.42 (dd, 1H), 5.82 (d, 1H), 7.25 (m, 1H), 7.38 (d, 1H)

PREPARATION EXAMPLE 3

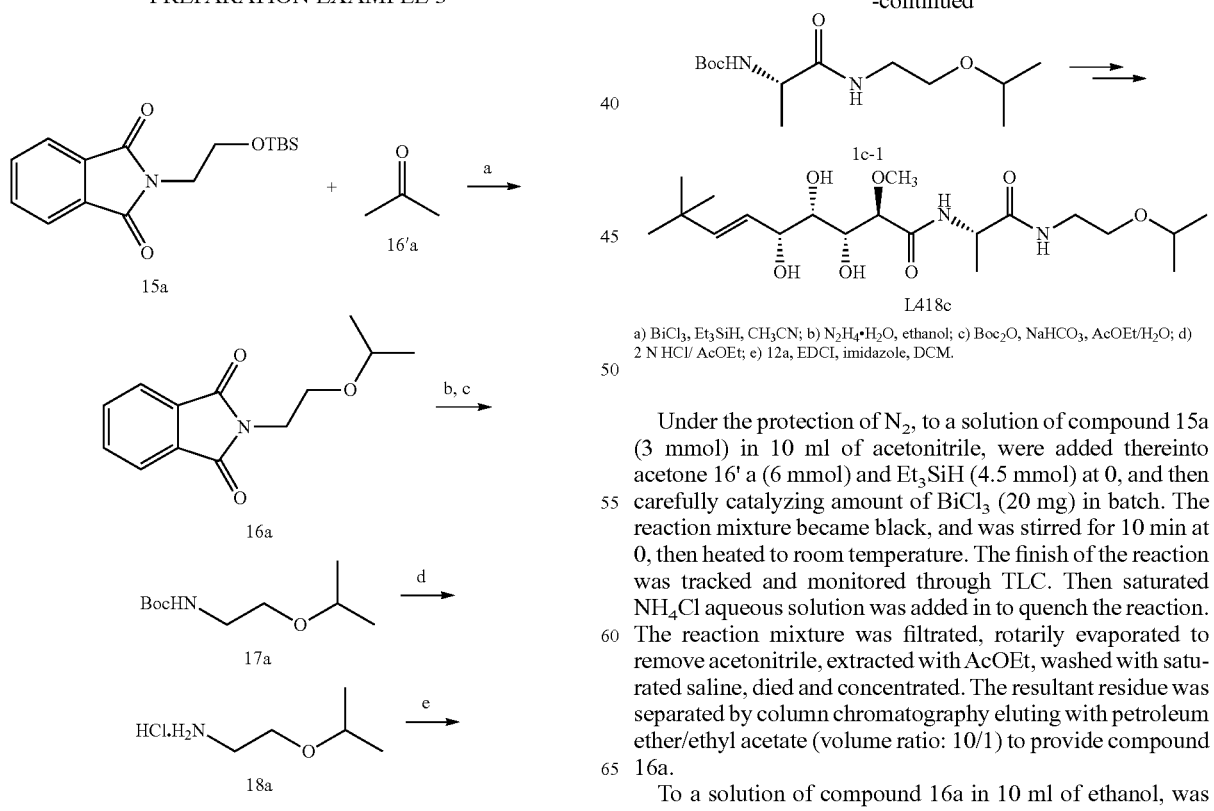

a) BiCl₃, Et₃SiH, CH₃CN; b) N₂H₄·H₂O, ethanol; c) Boc₂O, NaHCO₃, AcOEt/H₂O; d) 2 N HCl/ AcOEt; e) 12a, EDCI, imidazole, DCM.

Under the protection of N₂, to a solution of compound 15a (3 mmol) in 10 ml of acetonitrile, were added thereinto acetone 16' a (6 mmol) and Et₃SiH (4.5 mmol) at 0, and then carefully catalyzing amount of BiCl₃ (20 mg) in batch. The reaction mixture became black, and was stirred for 10 min at 0, then heated to room temperature. The finish of the reaction was tracked and monitored through TLC. Then saturated NH₄Cl aqueous solution was added in to quench the reaction. The reaction mixture was filtrated, rotarily evaporated to remove acetonitrile, extracted with AcOEt, washed with saturated saline, died and concentrated. The resultant residue was separated by column chromatography eluting with petroleum ether/ethyl acetate (volume ratio: 10/1) to provide compound 16a.

To a solution of compound 16a in 10 ml of ethanol, was added N₂H₄.H₂O (9 mmol), and the reaction mixture was heated to 80 and stirred for 3 h. Then a large amount of white solid appeared in the reaction mixture. The reaction mixture was cooled to room temperature, and acidified with concentrated hydrochloric acid to a pH of 1-2. After stirred for 1 h at room temperature, the reaction mixture was filtered and concentrated, into which were added 15 ml of H$_2$O, 15 ml of AcOEt, NaHCO$_3$ (6 mmol) and Boc$_2$O (6 mmol). After stirred overnight, the reaction mixture was extracted with AcOEt and separated. The organic phase was washed with saturated saline, died and concentrated. The resultant residue was separated by column chromatography eluting with petroleum ether/ethyl acetate (volume ratio: 10/1) to give compound 17a.

Compound 17a (1 mmol) was then dissolved in 2 ml of 2N HCl/AcOEt, and the mixture was stirred for 2 h at room temperature until the reaction was completed. Then, the reaction mixture was ratorily evaporated to dryness to remove solvent to afford compound 18a.

To a solution of 18a in 5 ml of dry dichloromethane, were added thereinto imidazole (1.5 mmol), compound 12a (1.5 mmol) and EDCI. After stirred at room temperature overnight, the reaction mixture was diluted with 30 ml of dichloromethane, washed with water and then with saturated saline, dried and concentrated. The resultant residue was separated by column chromatography eluting with petroleum ether/ethyl acetate (volume ratio: 5/1) to provide compound 1c-1.

The compound 1c-1 was treated according to the subsequent processes in Example 1 to provide compound L418c.

The target compounds in the following table 3 were produced with the same method as that in Preparation Example 3, expect various compound 16' instead of the compound 16'a and various compound 15 instead of the compound 15a, as listed in the following table 3:

TABLE 3

| No. | Compound 16' | Compound 15 | Target Compound |
|---|---|---|---|
| L418c |  | 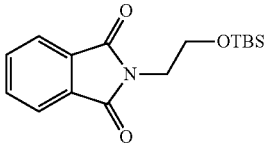 [SMILES: CC(C)(C)[Si](C)(C)OCCN1C(=O)c2ccccc2C1=O] | 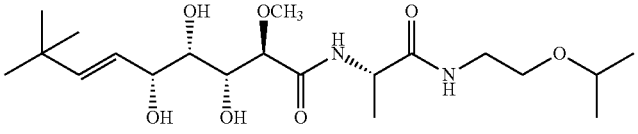 [SMILES: CO[C@@H](C(=O)N[C@@H](C)C(=O)NCCOC(C)C)[C@H](O)[C@@H](O)[C@H](O)/C=C/C(C)(C)C] |

$^1$H NMR (CDCl$_3$, 300 MHz) δ 1.03 (s, 9H), 1.15 (d, 6H), 1.43 (d, 3H), 3.04 (s, 1H), 3.40 (m, 2H), 3.0~3.40 (m, 5H), 3.60 (m, 1H), 3.65 (t, 2H), 3.80 (d, 1H), 3.90 (s, 1H), 4.10 (s, 1H), 4.20 (s, 1H), 4.43 (m, 1H), 5.42 (dd, 1H), 5.83 (d, 1H), 6.70 (m, 1H), 7.25 (d, 1H)

| | | | |
|---|---|---|---|
| L432a | 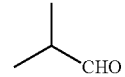 | 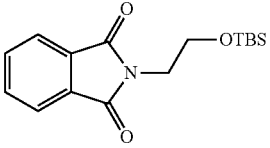 [SMILES: CC(C)(C)[Si](C)(C)OCCN1C(=O)c2ccccc2C1=O] | 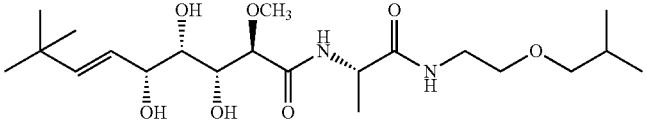 [SMILES: CO[C@@H](C(=O)N[C@@H](C)C(=O)NCCOCC(C)C)[C@H](O)[C@@H](O)[C@H](O)/C=C/C(C)(C)C] |

$^1$H NMR (CDCl$_3$, 300 MHz) δ 0.86 (d, 6H), 1.03 (s, 9H), 1.40 (d, 3H), 1.83 (m, 1H), 3.20 (m, 2H), 3.40 (m, 3H), 3.45 (s, 3H), 3.6 (s, 1H), 3.78 (d, 1H), 3.90 (s, 1H), 4.18 (s, 1H), 4.22 (s, 1H), 4.42 (m, 1H), 5.40 (dd, 1H), 5.80 (d, 1H), 6.98 (m, 1H), 7.28 (d, 1H)

| | | | |
|---|---|---|---|
| L458e | 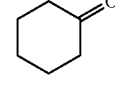 | 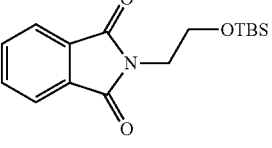 | 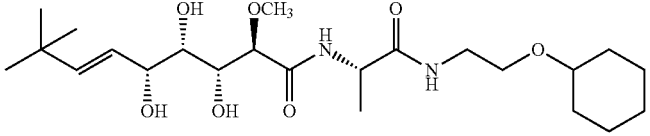 [SMILES: CO[C@@H](C(=O)N[C@@H](C)C(=O)NCCOC1CCCCC1)[C@H](O)[C@@H](O)[C@H](O)/C=C/C(C)(C)C] |

$^1$H NMR (CDCl$_3$, 300 MHz) δ 1.03 (s, 9H), 1.23 (m, 6H), 1.45 (d, 3H), 1.72 (m, 2H), 1.95 (m, 2H), 3.01 (s, 1H), 3.22 (m, 1H), 3.40 (m, 2H), 3.50 (s, 3H), 3.65~3.55 (m, 4H), 3.80 (d, 1H), 3.90 (s, 1H), 4.05 (d, 1H), 4.20 (m, 1H), 4.43 (m, 1H), 5.42 (dd, 1H), 5.82 (d, 1H), 6.65 (m, 1H), 7.24 (d, 1H)

| | | | |
|---|---|---|---|
| L432b |  | 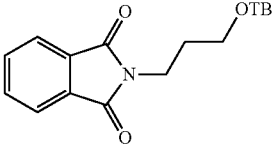 | 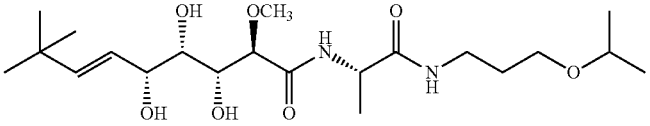 [SMILES: CO[C@@H](C(=O)N[C@@H](C)C(=O)NCCCOC(C)C)[C@H](O)[C@@H](O)[C@H](O)/C=C/C(C)(C)C] |

$^1$H NMR (CDCl$_3$, 300 MHz) δ 1.03 (s, 9H), 1.15 (d, 6H), 1.43 (d, 3H), 1.75 (m, 2H), 3.04 (s, 1H), 3.40 (m, 2H), 3.0~3.40 (m, 5H), 3.60 (m, 1H), 3.65 (t, 2H), 3.80 (d, 1H), 3.90 (s, 1H), 4.10 (s, 1H), 4.20 (s, 1H), 4.43 (m, 1H), 5.42 (dd, 1H), 5.83 (d, 1H), 6.85 (m, 1H), 7.28 (d, 1H)

TABLE 3-continued
| No. | Compound 16' | Compound 15 | Target Compound |
|---|---|---|---|
| L446b | 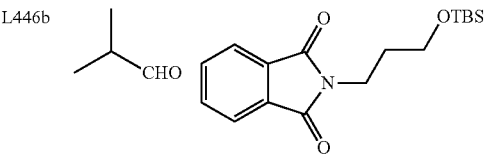 | 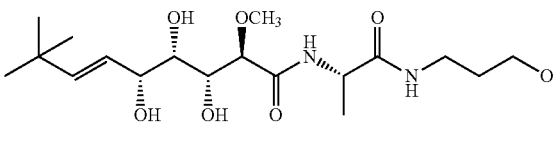 | 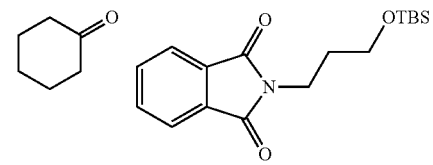 |
¹H NMR (CDCl₃, 300 MHz) δ 0.86 (d, 6H), 1.03 (s, 9H), 1.40 (d, 3H), 1.78 (m, 2H), 1.83 (m, 1H), 3.20 (m, 2H), 3.40 (m, 3H), 3.45 (s, 3H), 3.7 (s, 1H), 3.78 (d, 1H), 3.90 (s, 1H), 4.18 (s, 1H), 4.22 (s, 1H), 4.42 (m, 1H), 5.40 (dd, 1H), 5.80 (d, 1H), 6.98 (m, 1H), 7.28 (d, 1H)
| L472 | 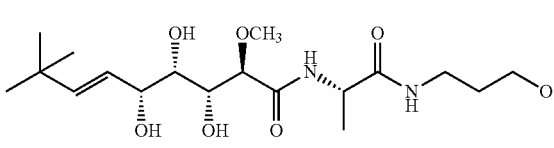 | | |
¹H NMR (CDCl₃, 300 MHz) δ 1.03 (s, 9H), 1.23 (m, 6H), 1.45 (d, 3H), 1.72 (m, 4H), 1.95 (m, 2H), 3.01 (s, 1H), 3.22 (m, 1H), 3.40 (m, 2H), 3.50 (s, 3H), 3.65~3.55 (m, 4H), 3.80 (d, 1H), 3.90 (s, 1H), 4.05 (d, 1H), 4.20 (m, 1H), 4.43 (m, 1H), 5.42 (dd, 1H), 5.82 (d, 1H), 6.93 (m, 1H), 7.32 (d, 1H)
| L466 | 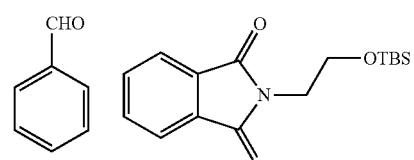 | | 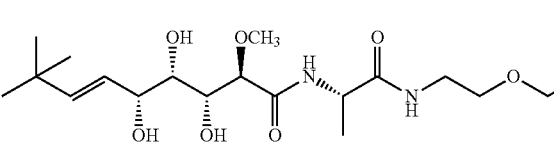 |
¹H NMR (CDCl₃, 300 MHz) δ 1.03 (s, 9H), 1.42 (d, 3H), 3.04 (m, 1H), 3.42 (m, 2H), 3.45 (s, 3H), 3.5 (m, 2H), 3.60 (m, 1H), 3.70 (m, 2H), 3.79 (d, 1H), 3.85 (s, 1H), 4.10 (m, 1H), 4.50 (s, 2H), 5.40 (dd, 1H), 5.79 (d, 1H), 6.92 (m, 1H), 7.05 (d, 1H), 7.31 (m, 5H).

PREPARATION EXAMPLE 4

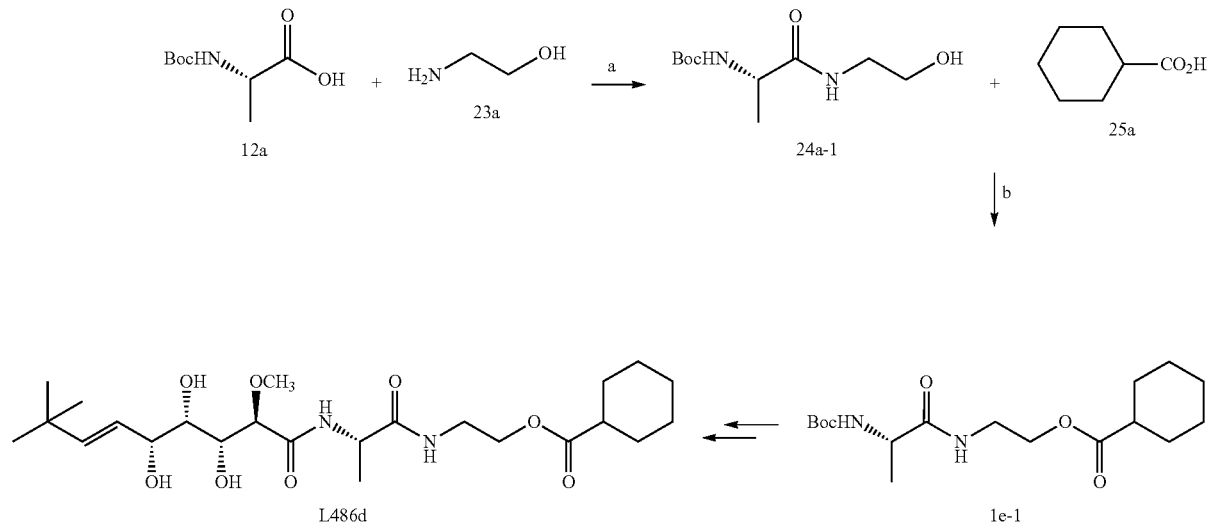

a) EDCI, imidazole, DCM; b) EDCI, DMAP, DCM.

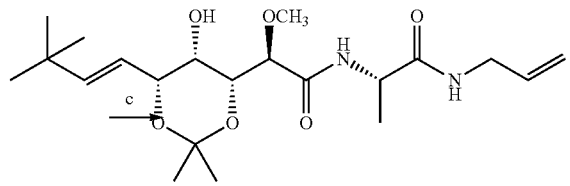

4a-1

Under $N_2$ atmosphere, to a solution of compound 12a (2 mmol) and 23a (2 mmol) in 10 ml dichloromethane, were added thereinto EDCI (3 mmol) and imidazole (3 mmol). After the reaction mixture was stirred overnight, the finish of the reaction was identified through TLC. The reaction mixture was then diluted with 30 ml dichloromethane, washed with saturated saline, died and concentrated. The resultant residue was separated by column chromatography eluting with chloroform/methanol (volume ratio: 50:1) to provide compound 24a-1.

To a solution of 24a-1 (1 mmol) in 10 ml of dichloromethane, were added thereinto carboxylic acid 25a (1 mmol), EDCI (1.5 mmol) and DMAP (catalyzing amount, 0.05 mmol). After the reaction mixture was stirred overnight, the finish of the reaction was identified by TLC. The reaction mixture was then diluted with 40 ml of dichloromethane, washed with saturated saline, died and concentrated. The resultant residue was separated by column chromatography eluting with petroleum ether/ethyl acetate (volume ratio: 3/1) to give compound 1e-1.

The compound 1e-1 was treated according to the subsequent processes in Example 1 to provide compound L486d.

The target compounds in the following table 4 were produced with the same method as that in Preparation Example 4, expect various compound 12 instead of the compound 12a and various compound 23 instead of the compound 23a, as listed in table 3:

TABLE 4

| No. | Compound 12 | Compound 23 | Compound 25 | Target Compound |
|---|---|---|---|---|
| L486d | BocHN-Ala-OH | HO-CH₂CH₂-NH₂ | Cyclohexane-CO₂H | ¹H NMR (CDCl₃, 300 MHz) δ 1.03 (s, 9H), 1.25 (m, 5H), 1.75 (d, 3H), 1.90 (m, 2H), 2.33 (m, 1H), 3.50 (s, 3H), 3.65 (s, 1H), 3.80 (d, 1H), 3.95d, 1H), 4.15 (t, 2H), 4.22 (m, 1H), 4.50 (m, 1H), 5.45 (dd, 1H), 5.92 (d, 1H), 6.80 (m, 1H), 7.19 (d, 1H) |
| L528a | BocHN-Ile-OH | HO-CH₂CH₂-NH₂ | Cyclohexane-CO₂H | ¹H NMR (CDCl₃, 300 MHz) δ 0.95 (m, 8H), 1.03 (s, 9H), 1.25 (m, 6H), 1.75 (m, 3H), 1.90 (m, 2H), 2.33 (m, 1H), 3.04 (d, 1H), 3.50 (s, 3H), 3.52 (m, 4H), 3.65 (s, 1H), 3.82 (d, 1H), 3.95 (d, 1H), 4.15 (m, 2H), 4.22 (m, 1H), 4.35 (m, 1H), 5.45 (dd, 1H), 5.92 (d, 1H), 6.70 (m, 1H), 7.19 (d, 1H) |
| L528b | BocHN-Leu-OH | HO-CH₂CH₂-NH₂ | Cyclohexane-CO₂H | ¹H NMR (CDCl₃, 300 MHz) δ 0.95 (m, 6H), 1.03 (s, 9H) 1.03~1.90 (m, 13H), 2.33 (m, 1H), 3.21 (s, 1H), 3.50 (s, 3H), 3.52 (m, 4H), 3.65 (s, 1H), 3.82 (d, 1H), 3.95 (s, 1H), 4.15 (t, 2H), 4.22 (m, 1H), 4.45 (m, 1H), 5.45 (dd, 1H), 5.92 (d, 1H), 6.93 (m, 1H), 7.07 (d, 1H) |

TABLE 4-continued

| No. | Compound 12 | Compound 23 | Compound 25 | Target Compound |
|---|---|---|---|---|
| L528c | | | | ¹H NMR (CDCl₃, 300 MHz) δ 0.90 (t, 3H), 1.03 (s, 9H), 1.25 (m, 11H) 1.75 (m, 3H), 1.90 (m, 2H), 2.33 (m, 1H), 3.04 (d, 1H), 3.50 (s, 3H), 3.52 (m, 4H), 3.65 (m, 2H), 3.95 (d, 1H), 4.15 (m, 2H), 4.22 (m, 1H), 4.38 (m, 1H), 5.45 (dd, 1H), 5.92 (d, 1H) |
| L514c | | | | ¹H NMR (CDCl₃, 300 MHz) δ 0.95 (m, 6H), 1.03 (s, 9H), 1.10~1.90 (m, 11H), 2.33 (m, 1H), 3.23 (s, 1H), 3.50 (s, 3H), 3.52 (m, 4H), 3.65 (s, 1H), 3.82 (d, 1H), 3.95 (s, 1H), 4.15 (t, 2H), 4.22 (m, 1H), 4.30 (m, 1H), 5.45 (dd, 1H), 5.92 (d, 1H), 6.73 (m, 1H), 7.19 (d, 1H) |
| L643 | | | | ¹H NMR (CDCl₃, 300 MHz) δ 1.03 (s, 9H), 1.20~1.90 (m, 18H), 1.42 (s, 9H), 2.33 (m, 1H), 3.13 (m, 2H), 3.50 (s, 3H), 3.52 (m, 1H), 3.65 (s, 1H), 3.75 (m, 1H), 3.82 (d, 1H), 3.95 (s, 1H), 4.15 (t, 2H), 4.22 (m, 1H), 4.40 (m, 1H), 4.65 (m, 1H), 5.45 (dd, 1H), 5.92 (d, 1H), 6.73 (m, 1H), 7.19 (d, 1H) |

TABLE 4-continued

| No. | Compound 12 | Compound 23 | Compound 25 | Target Compound |
|---|---|---|---|---|
| L485 | BocHN-Ala-OH | HO-CH₂CH₂-NH₂ | cyclohexane-CO₂H | $^1$H NMR (CDCl$_3$, 300 MHz) δ 1.03 (s, 9H), 1.25 (m, 5H), 1.75 (m, 3H), 1.90 (m, 2H), 2.08 (m, 1H), 3.50 (s, 3H), 3.48 (m, 5H), 3.85 (d, 1H), 4.05 (s, 2H), 4.10 (m, 2H), 4.50 (m, 1H), 5.45 (dd, 1H), 5.92 (d, 1H), 7.05 (d, 1H), 7.35 (m, 1H) |
| L500c | BocHN-Ala-OH | HO-CH₂CH₂-NH₂ | cyclohexyl-CH₂-CO₂H | $^1$H NMR (CDCl$_3$, 300 MHz) δ 1.03 (s, 9H), 1.25 (m, 5H), 1.45 (d, 3H), 1.75 (m, 6H), 2.33 (d, 1H), 3.12 (d, 1H), 3.50 (s, 3H), 3.52 (m, 2H), 3.65 (m, 1H), 3.80 (m, 2H), 3.98 (s, 1H), 4.18 (t, 2H), 4.22 (m, 1H), 4.50 (m, 1H), 5.45 (dd, 1H), 5.92 (d, 1H), 6.82 (m, 1H), 7.19 (d, 1H) |
| L484 | BocHN-Ala-OH | HO-CH₂CH₂-NH₂ | cyclohexenyl-CO₂H | $^1$H NMR (CDCl$_3$, 300 MHz) δ 1.03 (s, 9H), 1.25 (m, 5H), 1.45 (d, 3H), 1.70 (m, 2H), 2.10 (m, 2H), 2.25 (m, 2H), 2.60 (m, 1H), 3.08 (s, 1H), 3.50 (s, 3H), 3.52 (m, 3H), 3.65 (s, 1H), 3.80 (d, 2H), 3.98 (d, 1H), 4.19 (mt, 3H), 4.50 (m, 1H), 5.45 (dd, 1H), 5.68 (m, 2H), 5.92 (d, 1H), 6.80 (m, 1H), 7.19 (d, 1H) |
| L474 | BocHN-Ala-OH | HO-CH₂CH₂-NH₂ | (S)-tetrahydrofuran-2-CO₂H | $^1$H NMR (CDCl$_3$, 300 MHz) δ 11.03 (s, 9H), 1.24 (m, 4H), 1.45 (d, 3H), 2.10 (m, 2H), 3.20 (m, 2H), 3.50 (s, 3H), 3.42 (m, 4H), 4.80–4.60 (m, 4H), 4.08 (s, 1H), 4.21 (m, 1H), 4.50 (m, 2H), 5.45 (dd, 1H), 5.92 (d, 1H), 7.19 (m, 1H), 7.39 (d, 1H) |

TABLE 4-continued
| No. | Compound 12 | Compound 23 | Compound 25 | Target Compound |
|---|---|---|---|---|
| L472-3 | 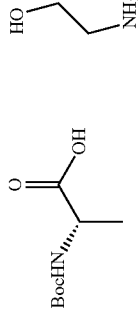 | 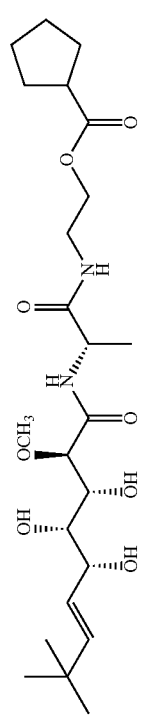 | 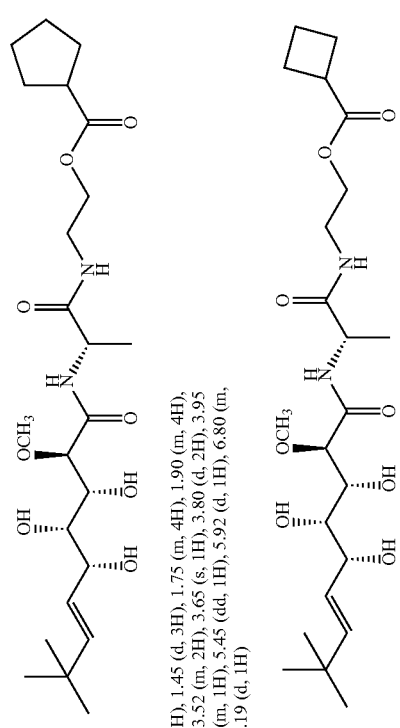 | 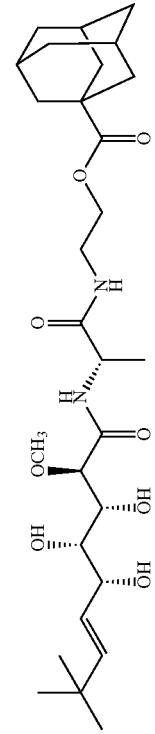<br>¹H NMR (CDCl₃, 300 MHz) δ 1.03 (s, 9H), 1.45 (d, 3H), 1.75 (m, 4H), 1.90 (m, 4H), 2.75 (m, 1H), 3.15 (d, 1H), 3.50 (s, 3H), 3.52 (m, 2H), 3.65 (s, 1H), 3.80 (d, 2H), 3.95 (m, 1H), 4.05 (m, 1H), 4.15 (t, 2H), 4.22 (m, 1H), 5.45 (dd, 1H), 5.92 (d, 1H), 6.80 (m, 1H), 7.19 (d, 1H) |
| L458 | 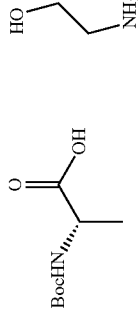 | 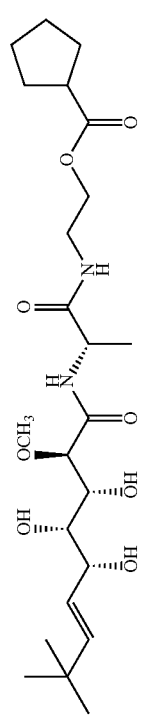 | 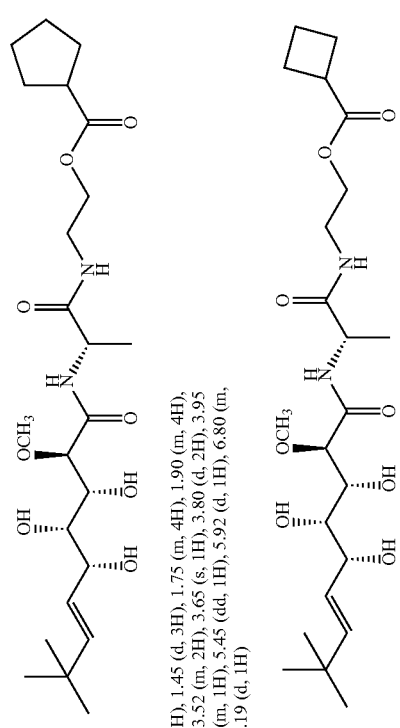 | 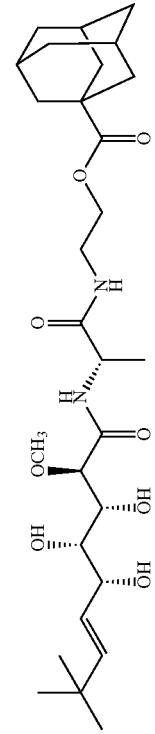<br>¹H NMR (CDCl₃, 300 MHz) δ 1.03 (s, 9H), 1.43 (d, 3H), 1.95 (m, 2H), 2.10 (m, 5H), 3.05 (d, 1H), 3.50 (s, 3H), 3.52 (m, 3H), 3.65 (s, 1H), 3.80 (t, 2H), 3.95 (m, 1H), 4.15 (t, 2H), 4.22 (m, 1H), 4.45 (m, 1H), 5.45 (dd, 1H), 5.92 (d, 1H), 6.80 (m, 1H), 7.19 (d, 1H) |
| L444g | 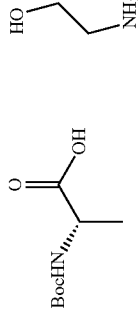 | 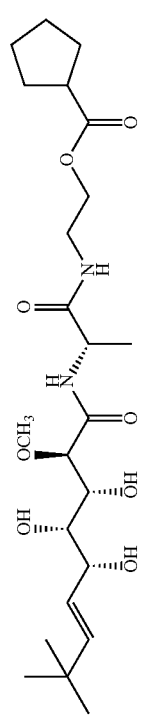 | 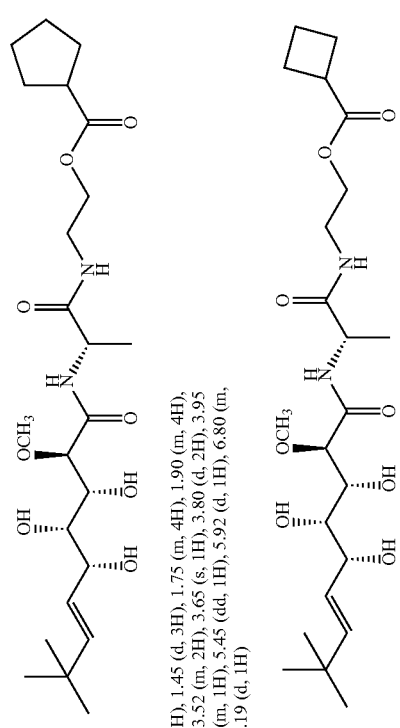 | 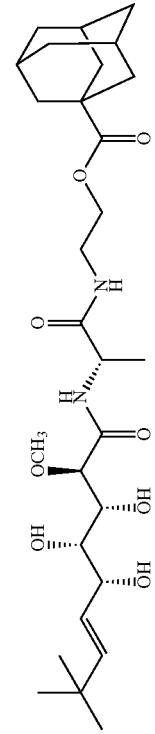<br>¹H NMR (CDCl₃, 300 MHz) δ 0.90 (m, 4H), 1.03 (s, 9H), 1.43 (d, 3H), 1.65 (m, 1H), 3.05 (d, 1H), 3.50 (s, 3H), 3.52 (m, 3H), 3.65 (s, 1H), 3.80 (m, 2H), 3.95 (m, 1H), 4.15 (t, 2H), 4.22 (m, 1H), 4.45 (m, 1H), 5.45 (dd, 1H), 5.92 (d, 1H), 6.80 (m, 1H), 7.19 (d, 1H) |
| L538 | 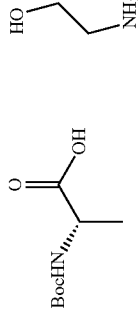 | 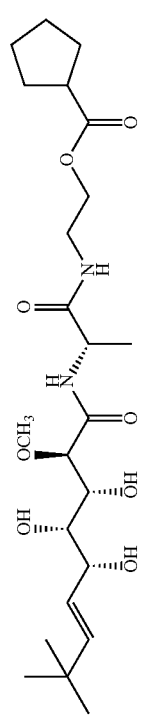 | 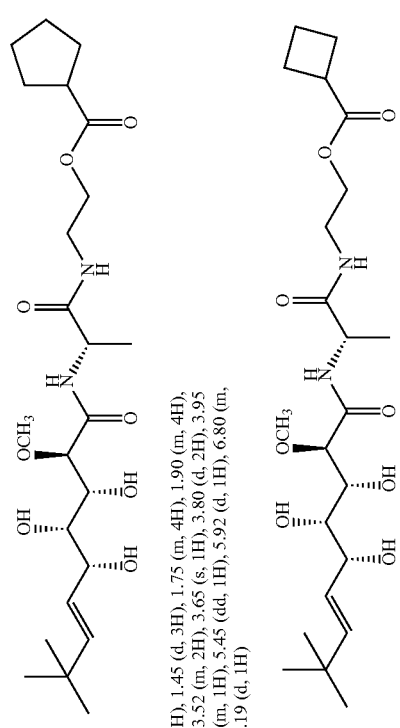 | 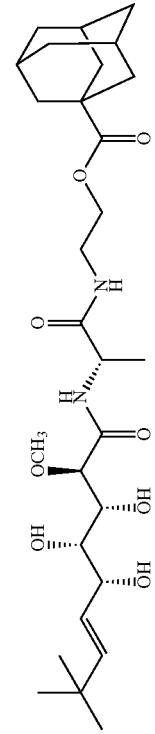<br>¹H NMR (CDCl₃, 300 MHz) δ 1.03 (s, 9H), 1.43 (d, 3H), 1.70 (m, 6H), 1.85 (m, 7H), 2.00 (m, 2H), 3.20 (d, 1H), 3.50 (s, 3H), 3.52 (m, 2H), 3.65 (s, 1H), 3.80 (d, 2H), 3.95 (m, 1H), 4.15 (t, 2H), 4.22 (m, 2H), 4.45 (m, 1H), 5.45 (dd, 1H), 5.82 (d, 1H), 6.80 (m, 1H), 7.20 (d, 1H) |

TABLE 4-continued

| No. | Compound 12 | Compound 23 | Compound 25 | Target Compound |
|---|---|---|---|---|
| L480 | BocHN-Ala-OH | HO-CH2CH2-NH2 | PhCO2H | ¹H NMR (CDCl₃, 300 MHz) δ 1.03 (s, 9H), 1.43 (d, 3H), 3.15 (m, 1H), 3.43 (s, 3H), 3.45 (m, 1H), 3.63 (m, 2H), 3.80 (m, 2H), 3.95 (m, 1H), 4.15 (m, 2H), 4.40 (t, 2H), 4.52 (m, 1H), 5.43 (dd, 1H), 5.80 (d, 1H), 7.03 (m, 1H), 7.21 (d, 1H), 7.43 (m, 2H), 7.60 (m, 1H), 8.05 (m, 2H). |
| L508 | BocHN-Ala-OH | HO-CH2CH2-NH2 | HO2C-CH2CH2-Ph | ¹H NMR (CDCl₃, 300 MHz) δ 1.03 (s, 9H), 1.40 (d, 3H), 2.65 (t, 2H), 2.95 (t, 2H), 3.10 (m, 1H), 3.43 (s, 3H), 3.45 (m, 2H), 3.63 (m, 1H), 3.80 (m, 2H), 3.95 (m, 1H), 4.15 (m, 2H), 4.20 (m, 2H), 4.42 (m, 1H), 5.43 (dd, 1H), 5.80 (d, 1H), 6.63 (m, 1H), 7.20 (m, 4H), 7.26 (m, 2H). |
| L500a | BocHN-Ala-OH | HO-CH(CH3)CH2-NH2 | Cyclohexyl-CO2H | ¹H NMR (CDCl₃, 300 MHz) δ 1.03 (s, 9H), 1.20 (d, 3H), 1.30 (m, 4H), 1.41 (d, 3H), 1.70 (m, 3H), 1.90 (m, 3H), 2.25 (m, 1H), 3.12 (d, 1H), 3.20 (d, 1H), 3.30 (m, 1H), 3.41 (m, 1H), 3.45 (s, 3H), 3.65 (s, 1H), 3.80 (s, 1H), 3.95 (m, 1H), 4.15 (m, 1H), 4.21 (m, 1H), 4.45 (m, 1H), 4.95 (m, 1H), 5.45 (dd, 1H), 5.92 (m, 1H), 6.71 (d, 1H), 7.18 (m, 1H) |

TABLE 4-continued

| No. | Compound 12 | Compound 23 | Compound 25 | Target Compound |
|---|---|---|---|---|
| L500b | BocHN-Ala-OH | HO-(CH2)3-NH2 | Cyclohexane-CO2H | Structure shown. ¹H NMR (CDCl₃, 300 MHz) δ 1.03 (s, 9H), 1.29 (m, 4H), 1.42 (d, 3H), 1.80 (m, 8H), 2.30 (m, 1H), 3.20 (d, 2H), 3.35 (m, 1H), 3.46 (s, 3H), 3.68 (s, 1H), 3.93 (d, 1H), 3.98 (m, 2H), 4.10 (t, 2H), 4.20 (m, 2H), 4.45 (m, 1H), 5.45 (dd, 1H), 5.82 (m, 1H), 6.83 (m, 1H), 7.18 (d, 1H). |
| L558a | BocHN-Ala-OH | Serine ethyl ester | Cyclohexane-CO2H | Structure shown. ¹H NMR (CDCl₃, 300 MHz) δ 1.03 (s, 9H), 1.25 (t, 3H), 1.30 (m, 4H), 1.42 (d, 3H), 1.70 (m, 3H), 1.85 (m, 3H), 2.30 (m, 1H), 3.05 (dd, 1H), 3.45 (s, 3H), 3.63 (m, 2H), 3.90 (d, 1H), 3.95 (d, 1H), 4.08 (m, 1H), 4.20 (m, 3H), 4.35 (d, 1H), 4.40 (d, 1H), 4.55 (m, 1H), 4.80 (m, 1H), 5.42 (dd, 1H), 5.82 (d, 1H), 7.11 (d, 1H), 7.20 (m, 1H). |
| L502 | BocHN-Ala-OH | HO-CH2CH2-NH2 | 2-ethylhexanoic acid | Structure shown. ¹H NMR (CDCl₃, 300 MHz) δ 0.85 (t, 6H), 1.03 (s, 9H), 1.25 (m, 3H), 1.42 (d, 3H), 1.55 (m, 3H), 2.24 (m, 1H), 3.15 (s, 1H), 3.45 (s, 3H), 3.48 (m, 2H), 3.65 (s, 1H), 3.72 (s, 1H), 3.90 (d, 1H), 3.95 (m, 1H), 4.15 (m, 1H), 4.20 (m, 2H), 4.45 (m, 1H), 5.83 (d, 1H), 6.80 (m, 1H), 7.20 (d, 1H). |

TABLE 4-continued

| No. | Compound 12 | Compound 23 | Compound 25 | Target Compound |
|---|---|---|---|---|
| L586 | BocHN-Ala-OH | HO-CH2CH2-NH2 | HOOC-(CH2)11-CH3 | ¹H NMR (CDCl₃, 300 MHz) δ 0.85 (t, 3H), 1.03 (s, 9H), 1.25 (m, 20H), 2.41 (d, 3H), 1.60 (m, 2H), 2.28 (t, 2H), 3.45 (s, 3H), 3.44 (m, 4H), 3.65 (s, 1H), 3.80 (s, 1H), 3.95 (s, 1H), 4.15 (t, 2H), 4.20 (m, 2H), 4.45 (m, 1H), 5.42 (dd, 1H), 5.81 (d, 1H), 6.80 (m, 1H), 7.19 (d, 1H). |
| L446a | BocHN-Ala-OH | HO-CH2CH2-NH2 | iBu-CO2H | ¹H NMR (CDCl₃, 300 MHz) δ 1.03 (s, 9H), 1.19 (d, 6H), 1.41 (d, 3H), 2.55 (m, 1H), 3.19 (s, 1H), 3.45 (s, 3H), 3.44 (m, 2H), 3.62 (s, 1H), 3.80 (m, 2H), 3.95 (m, 1H), 4.15 (m, 2H), 4.20 (m, 2H), 4.50 (m, 1H), 5.42 (dd, 1H), 5.80 (d, 1H), 6.85 (m, 1H), 7.20 (d, 1H). |
| L460 | BocHN-Ala-OH | HO-CH2CH2-NH2 | tBu-CO2H | ¹H NMR (CDCl₃, 300 MHz) δ 1.03 (s, 9H), 1.19 (s, 9H), 1.41 (d, 3H), 3.10 (s, 1H), 3.45 (s, 3H), 3.50 (m, 3H), 3.60 (s, 1H), 3.72 (s, 1H), 3.80 (d, 1H), 3.95 (s, 1H), 4.15 (m, 2H), 4.20 (m, 1H), 4.30 (m, 1H), 5.42 (dd, 1H), 5.81 (d, 1H), 6.78 (m, 1H), 7.16 (d, 1H). |
| L474b | BocHN-Ala-OH | HO-CH2CH2-NH2 | HOOC-(CH2)3-CH3 | ¹H NMR (CDCl₃, 300 MHz) δ 0.86 (t, 3H), 1.03 (s, 9H), 1.29 (m, 4H), 1.42 (d, 3H), 1.60 (m, 2H), 2.30 (t, 2H), 3.17 (s, 1H), 3.43 (s, 3H), 3.44 (m, 3H), 3.62 (m, 1H), 3.80 (t, 2H), 3.95 (m, 1H), 4.15 (m, 2H), 4.20 (m, 1H), 4.43 (m, 1H), 5.43 (dd, 1H), 5.80 (d, 1H), 6.85 (m, 1H), 7.20 (d, 1H). |

TABLE 4-continued

| No. | Compound 12 | Compound 23 | Compound 25 | Target Compound |
|---|---|---|---|---|
| L587 | | | | ¹H NMR (CDCl₃, 300 MHz) δ 0.85 (t, 3H), 1.03 (s, 9H), 1.25 (m, 19H), 1.44 (d, 3H), 1.60 (m, 4H), 2.32 (t, 2H), 3.00 (d, 1H), 3.67 (m, 5H), 3.74 (d, 1H), 3.80 (d, 1H), 3.97 (m, 1H), 4.08 (d, 1H), 4.15 (t, 2H), 4.24 (m, 1H), 4.48 (m, 1H), 5.46 (dd, 1H), 5.83 (d, 1H), 6.74 (m, 1H), 7.15 (d, 1H). |
| L541 | | | | ¹H NMR (CDCl₃, 300 MHz) δ 0.85 (t, 3H), 1.02 (s, 9H), 1.30 (m, 7H), 1.40 (d, 3H), 1.42-1.62 (m, 5H), 1.71 (s, 1H), 2.18 (ddd, 1H), 2.32 (t, 2H), 3.02 (d, 1H), 3.50 (m, 5H), 3.66 (m, 1H), 3.77 (dd, 2H), 3.97 (m, 1H), 4.08 (d, 1H), 4.14 (t, 2H), 4.22 (m, 1H), 4.48 (m, 1H), 5.46 (dd, 1H), 5.82 (d, 1H), 6.78 (m, 1H), 7.16 (m, 1H). |
| L471b | | | | ¹H NMR (CDCl₃, 300 MHz) δ 0.85 (m, 3H), 1.03 (s, 9H), 1.45 (d, 3H), 1.84 (m, 2H), 2.27 (m, 2H), 2.48 (t, 2H), 2.99 (m, 1H), 3.51 (s, 3H), 3.67 (m, 1H), 3.80 (m, 2H), 3.98 (m, 1H), 4.08 (m, 1H), 4.17 (t, 2H), 4.23 (m, 1H), 4.49 (m, 1H), 5.49 (dd, 1H), 5.83 (d, 1H), 6.76 (m, 1H), 7.14 (d, 1H). |
| L572 | | | | ¹H NMR (CDCl₃, 300 MHz) δ 1.02 (s, 9H), 1.21-1.28 (m, 10H), 1.42 (d, 3H), 1.61 (m, 4H), 2.31 (t, 2H), 3.25 (t, 2H), 3.49 (m, 4H), 3.61 (m, 1H), 3.79 (m, 1H), 3.97 (m, 1H), 4.14 (t, 2H), 4.20 (m, 1H), 4.44 (m, 1H), 5.42 (dd, 1H), 5.81 (d, 1H), 6.81 (d, 1H), 7.18 (d, 1H). |

PREPARATION EXAMPLE 5

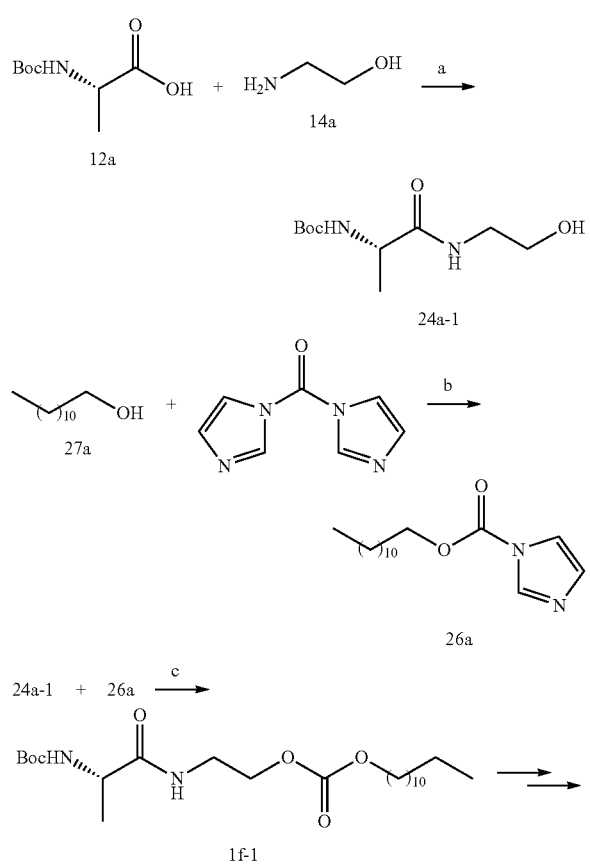

a) EDCI, imidazole, DCM; b) KOH, toluene; c) DBU, toluene.

The compound 24a-1 was prepared according to the Preparation Example 4.

The compound 26a was prepared as follows: at room temperature, N,N'-carbonylic diimidazole (1.1 mmol) and KOH (0.006 mmol) were added in a single-necked flask containing 10 ml of dry toluene, and stirred for 10 min. A solution of the compound 27a (1 mmol) in 1 ml of toluene was added slowly. The reaction system was then stirred for 30 min, and moved into an oil bath at 60. 8 h later, the finish of the reaction was identified by TLC.

The reaction solution of the above said compound 26a was cooled to room temperature, and compound 24a-1 (1.0 mmol) and 1.8-diazabicyclo[5.4.0]undec-7-ene (DBU, 0.15 mmol) were added thereinto and stirred. After the mixture was reacted for 10 h at room temperature, TLC analysis showed that the raw materials had been transformed completely. The reaction mixture was then concentrated to dryness by rotary evaporation, and the resultant residue was purified by column chromatography to afford compound 1f-1.

The compound 1f-1 was treated according to the subsequent processes in Preparation Example 1 to provide compound L589.

The target compounds in the following table 5 were produced with the same method as that in Preparation Example 5, expect various compound 27 listed in table 5 instead of the compound 27a.

TABLE 5

| No. | Compound 27 | Target Compound |
|---|---|---|
| L589 | ~~~~~~~~~~OH | (structure shown) |

$^1$H NMR (CDCl$_3$, 300 MHz) δ 0.85 (t, 3H), 1.03 (s, 9H), 1.25 (m, 20H), 1.45 (d, 3H), 3.09 (m, 1H), 3.49-3.41 (m, 4H), 3.62-3.54 (m, 1H), 3.70 (m, 1H), 3.86-3.82 (m, 2H), 3.99 (m, 1H), 4.09 (m, 1H), 4.20-4.11 (m, 5H), 4.50 (m, 1H), 5.47 (dd, 1H), 5.82 (d, 1H), 6.99 (m, 1H), 7.12 (d, 1H)

| L502b | cyclohexanol-OH | (structure shown) |

$^1$H NMR (CDCl$_3$, 300 MHz) δ 1.03 (s, 9H), 1.45 (d, 3H), 1.90~1.20 (m, 10H), 3.06 (m, 1H), 3.49-3.40 (m, 4H), 3.61-3.52 (m, 1H), 3.69 (m, 1H), 3.87~3.82 (m, 2H), 4.08 (m, 1H), 4.21-4.13 (m, 4H), 4.52 (m, 1H), 5.45 (dd, 1H), 5.84 (d, 1H), 7.01 (m, 1H), 7.14 (d, 1H)

| L538b | Ph(CH$_2$)$_3$OH | (structure shown) |

$^1$H NMR (CDCl$_3$, 300 MHz) δ 1.02 (s, 9H), 1.46 (d, 3H), 2.03 (quin, 2H), 2.71 (t, 2H), 3.05 (m, 1H), 3.49-3.42 (m, 4H), 3.59 (m, 1H), 3.68 (m, 1H), 3.87-3.82 (m, 2H), 4.00 (m, 1H), 4.07 (m, 1H), 4.21~4.16 (m, 4H), 4.51 (m, 1H), 5.46 (dd, 1H), 5.82 (d, 1H), 6.98 (m, 1H), 7.32-7.12 (m, 5H)

PREPARATION EXAMPLE 6

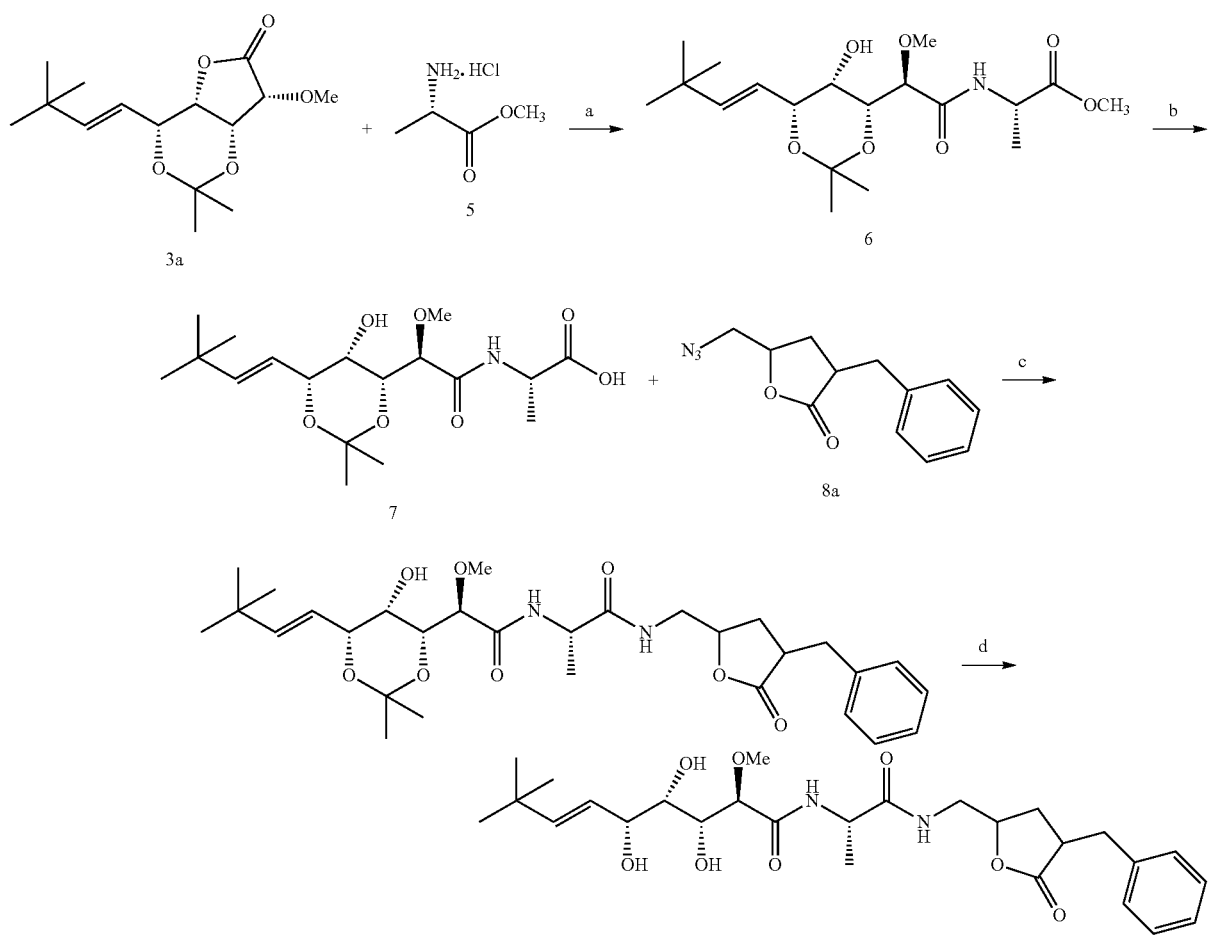

a) NaEH, THF; b) K₂CO₃, MeOH/H₂O; c) PPh₃, toluene; d) 1 N HCl/H₂O.

To a solution of the lactone compound 3a (1 mmol) in 5 ml of tetrahydrofuran, were added thereinto alanine methyl ester hydrochloride 5 (2 mmol) and sodium isocaprylate (4 mmol). After stirred for a while, the reaction system was moved into an oil bath at 50° C., and stirred for 30 h. The mixture was then concentrated to dryness by rotary evaporation. The residue was diluted with 30 ml of chloroform, extracted, washed with water and then with saturated saline, died, separated by column chromatography eluting with pure chloroform to provide coupled product 6.

The coupled product 6 (1 mmol) was dissolved in 6 ml of methanol, and a solution of K₂CO₃ (2 mmol) in 1 ml of H₂O was added thereinto at room temperature. After the reaction mixture was stirred for 4 h at room temperature, TLC analysis showed that the transformation had been completed. Post-treatment: the reaction mixture was concentrated to dryness through rotary evaporation, and a solution of 10 mmol NH₄Cl in 1 ml H₂O was added into the residue under ice bath. After stirred for a while, the mixture was filtered and concentrated. The residue was purified by column chromatography eluting with chloroform/methanol (volume ratio: about 4:1) to provide compound 7.

To a solution of compound 7 (1 mmol) in 5 ml of toluene, were added thereinto compound 8a (1 mmol) and PPh₃ (1 mmol) at room temperature. After stirred for a while, the reaction system was moved in an oil bath at 50° C. and stirred for 20 h. Post-treatment: After the solvent was removed by rotary evaporation, the residue was dissolved in 30 ml of chloroform. The solution was then transferred into a separating funnel, and washed with saturated NaHCO₃ aqueous solution, water and saturated saline in order, dried and concentrated. The residue was separated by column chromatography eluting with chloroform/methanol (volume ratio: about 100/1) to provide compound 9a.

Compound 9a was dissolved in 1 ml of THF, and 1 ml of 1N HCl was added thereinto. After the reaction mixture was stirred for 1.5 h at room temperature, TLC analysis showed that the transformation had been completed. Then, the reaction mixture was neutralized with 1 ml of aqueous ammonia under ice bath, and concentrated to dryness through rotary evaporation to remove solvent. The residue was separated by column chromatography eluting with chloroform/methanol (volume ratio: about 50:1) to provide target product L521.

¹H NMR (CDCl₃, 300 MHz): δ 0.88 (m, 3H), 1.03 (s, 9H), 1.64 (m, 4H), 2.04 (m, 1H), 2.28 (m, 1H), 2.78 (m, 2H), 2.98 (m, 2H), 3.14-3.32 (m, 3H), 3.45 (s, 1H), 3.51 (s, 3H), 3.60-3.80 (3H), 4.22 (m, 1H), 4.44 (m, 1H), 5.42 (m, 1H), 5.83 (d, 1H), 7.18 (m, 2H), 7.28 (m, 3H).

The Preparation of Intermediate 8a:

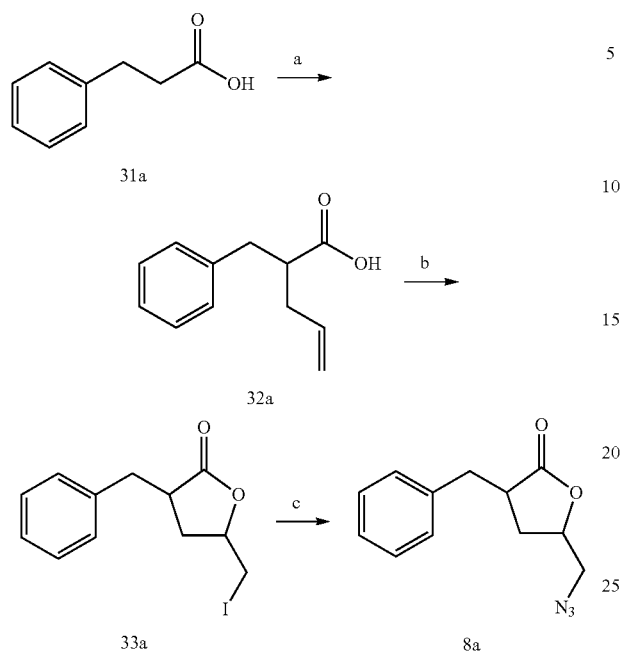

a) LDA, THF, allyl bromide; b) I₂, KI/H₂O, NaHCO₃, Et₂O; c) NaN₃, DMF, 50° C.

To a solution of diisopropylamine (2 mmol) in 10 ml of dry THF, was added thereinto a solution of 2 mmol n-butyl lithium in n-hexane under ice bath. The reaction mixture was stirred for 1 h under ice bath to provide a lithium diisopropylamide (LDA) reagent. To the prepared LDA solution, was added dropwise a solution of 1 mmol phenylpropionic acid 31a in 5 ml of tetrahydrofuran under ice bath. After the addition, the reaction mixture was stirred for 40 min under ice bath, and then allyl bromide (1.1 mmol) was added thereinto. The reaction mixture was further stirred under ice bath until the temperature thereof naturally rose to room temperature. Ten hours later, TLC analysis showed that the transformation had been completed. Posttreatment: The reaction mixture was diluted with 30 ml of ethyl acetate, and acidized with a 3N solution of hydrochloric acid through dropwise addition until the pH of the reaction system was 2. The organic layer was then separated, washed with water and then with saturated saline, died and concentrated. The residue was separated by column chromatography eluting with petroleum ether/ethyl acetate (volume ratio: about 10:1) to give compound 32a.

Compound 32a (1 mmol) was dissolved in 3 ml of ether, and 2 ml of 0.5 M NaHCO₃ aqueous solution was added thereinto. After the mixture was stirred for 1 h, 2 ml of an aqueous solution of I₂ (1.5 mmol) and KI (5 mmol) was added dropwise at room temperature, The stirring then continued for 2 h at room temperature, and TLC analysis showed that the raw materials had been exhausted. Posttreatment: The reaction mixture was diluted and extracted with 30 ml of ethyl ether. The organic layer was then washed with 5% Na₂S₂O₃ solution and saturated saline, died, and separated by column chromatography eluting with petroleum ether/acetone (volume ratio: about 15:1) to afford compound 33a, which is a mixture of two diastereomer that can not be separated.

Compound 33a (1 mmol) was dissolved in 3 ml of dry DMF, and NaN₃ (10 mmol) was added thereinto at room temperature. After stirred for a while, the reaction mixture was heated to 50° C. for 6 h. Posttreatment: The reaction mixture was diluted with 20 ml of ethyl acetate, washed with water and then with saturated saline, died and concentrated. The resultant residue was separated by column chromatography eluting with petroleum ether/acetone (volume ratio: about 15:1) to provide compound 8a.

PREPARATION EXAMPLE 7

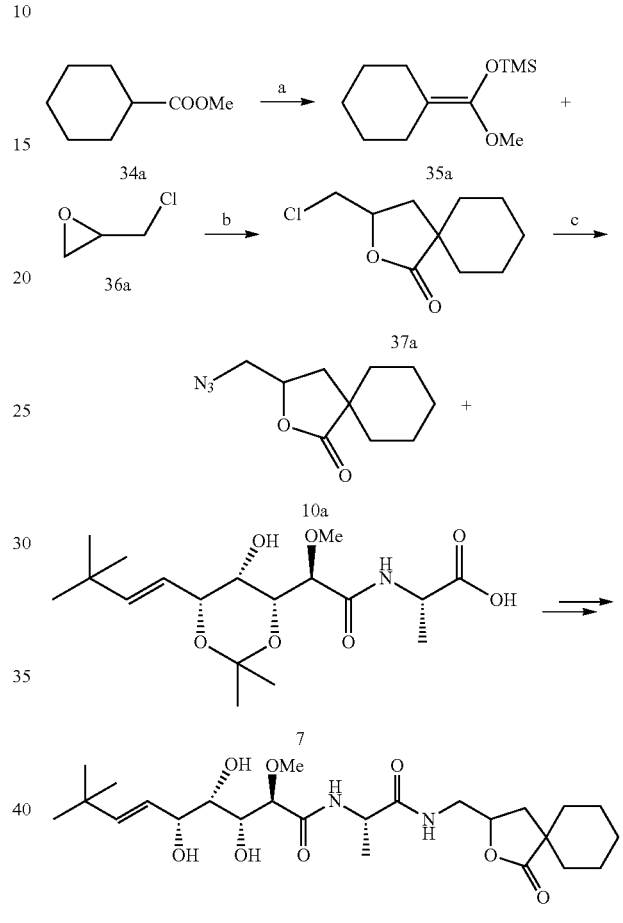

a) LDA, THF, TMSCl; b) dichloromethane/petroleum ether (V/V = 1/2), TiCl₄, p-toluenesulfonic acid; c) NaI, DMF, NaN₃.

For the preparation of compound 37a, reference is made to *Tetrahedron*, 2004, 60, 8957-8966.

To a solution of compound 37a (1 mmol) in 3 ml of dimethyl formamide, were added thereinto NaN₃ (10 mmol) and NaI (1 mmol) under stirring. The reaction mixture was then heated to 80° C. for 16 h. Posttreatment: The reaction mixture was diluted and extracted with 50 ml of chloroform, washed with water and then with saturated saline, died and concentrated. The resultant residue was purified by column chromatography eluting with petroleum ether/acetone (V/V=60:1) to provide compound 10a.

Compound L498c was produced with the same methods as those for preparing compounds 9a and L521 in Preparation Example 6.

¹H NMR (CDCl₃, 300 MHz): δ 1.02 (s, 9H), 1.23-1.81 (m, 12H), 2.33 (m, 1H), 2.99 (m, 1H), 3.31 (m, 2H), 3.46 (m, 4H), 3.51 (m, 1H), 3.79-3.82 (m, 3H), 4.00 (d, 1H), 4.21 (m, 1H), 4.51 (m, 1H), 5.42 (dd, 1H), 5.84 (d, 1H), 7.23 (m, 1H).

PREPARATION EXAMPLE 8

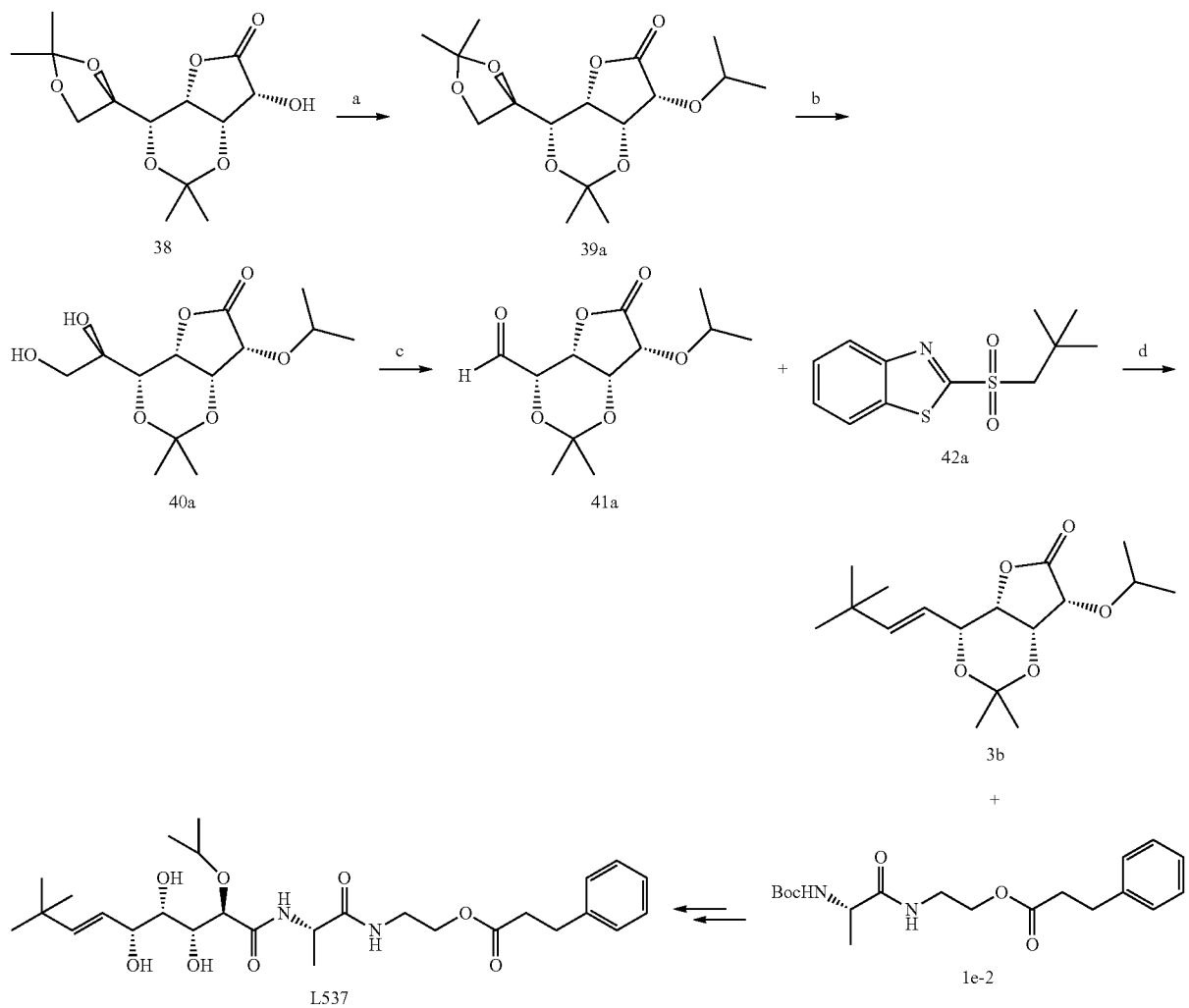

a) (CH$_3$)$_2$CH$_2$I, Ag$_2$O, DCM; b) C$_2$H$_5$COOH/H$_2$O, p-toluene sulfonic acid, isopropyl acetate; c) NaIO$_4$, MeCN/H$_2$O; d) n-BuLi, THF/CH$_3$CN, then TMSCl, then H$_2$O.

To a solution of compound 38 (1 mmol) in 8 ml of dichloromethane under nitrogen atmosphere, were rapidly added thereinto (CH$_3$)$_2$CH$_2$I (3 mmol) and Ag$_2$O (2 mmol), followed by the addition of 0.5 ml of H$_2$O. The reaction system was kept at a temperature of about 25° C., and stirred for 12 h under a dark environment. TLC analysis showed that the transformation had been completed. Posttreatment: The reaction mixture was diluted with 100 ml of dichloromethane, filtered, and concentrated to provide compound 39a.

To a solution of compound 39a (1 mmol) in a mixture of 50 ml isopropyl acetate and 25 ml of propionic acid, after the addition of 2 ml of H$_2$O, was added thereinto under stirring a solution of p-toluenesulfonic acid (2 mg, catalyzing amount) in 0.2 ml of H$_2$O under nitrogen atmosphere. Then, the reaction mixture was heated to 40° C. for 2 h. After the heating ceased, the reaction mixture was transferred in an ice bath at about 4° C., stirred slowly for 1 h and then filtered. The filter cake was washed with cold isopropyl acetate (2×10 ml), and dried to remove the solvent by using an oil pump to provide compound 40a.

Compound 40a (1 mmol) was inputted into a 100 ml two-necked flask, and 7.6 ml of acetonitrile and 3.5 ml of H$_2$O were added thereinto. The reaction mixture was stirred at room temperature until the solution became clear. After temperature of the reaction mixture was adjusted to below 5° C. by placing the reaction system under an ice bath, NaIO$_4$ (1.1 mmol) was added slowly thereinto while the temperature of the system was maintained between 5° C. and 10° C. After the addition, the reaction system was sealed under argon atmosphere, and stirred vigorously for 1 h while maintaining the temperature. Then, the reaction mixture was diluted with 5 ml of MeCN and 15 ml of isopropyl acetate, and 400 mg of anhydrous magnesium sulfate was added in while keeping the temperature of the system at about 8° C. 85 mg of solid NaHCO$_3$ was added in, and 900 mg of magnesium sulfate was added in immediately to take up water again. The reaction mixture was again stirred for 1 h at room temperature, and 500 mg of magnesium sulfate was added thereinto. The suspension was kept at room temperature and stirred for 1 h, then subjected to the post-treatments. After the reaction mixture was filtered, the filter cake was washed with a mixture of CH$_3$CN:i-PrOAc=1:3 (2×15 ml). The filtrate was concentrated, and separated by rapid column chromatography to provide compound 41a.

In a cryogenic flask, the compound 42a (1.0 mmol) was dissolved in 10 ml of dry tetrahydrofuran. After sealed, the flask was placed in an ice bath at −55 under argon atmosphere, and the stirring was performed for 10 min. A solution of n-butyllithium (1M in n-hexane, 1.1 mmol) was then dropwise added thereinto, and the temperature of the reaction system was dropped to −78° C. to react for 1.5 h. After the dropwise addition of TMSCl (1.1 mmol) the reaction mixture was kept at −78° C. and stirred for 25 min. To a 100 ml single-necked flask, were added thereinto compound 41a (0.9 mmol), NaHCO$_3$ (4 mg) and 40 ml dry CH$_3$CN, and the mixture was stirred under a cryohydric bath and argon atmosphere. The reaction mixture in the above cryogenic flask was then transferred into the single-necked flask. The reaction mixture was then stirred under the cryohydric bath for 25 min, and then under an ice bath for 1 h. After the temperature of the reaction mixture was raised to room temperature slowly, the reaction mixture was stirred for 1 h at that temperature, and then heated under an oil bath to rise to 40° C. slowly. After the reaction mixture was stirred at the temperature for 2 h, a slight amount of H$_2$O was added in to quench the reaction. The solvent thereof was then removed by rotary evaporation, and the residue was diluted with chloroform (150 ml), extracted, washed with water (2×20 ml) and then with saturated saline (2×20 ml), dried over anhydrous sodium sulfate and concentrated. The residue was separated by column chromatography to provide compound 3b.

According to the subsequent processes in Example 1, compound 3b reacted with compound 1e-2, and then deprotected to afford compound L537.

$^1$H NMR (CDCl$_3$, 300 MHz): δ 1.03 (s, 9H), 1.18 (m, 6H), 1.40 (d, 3H), 2.64 (t, 2H), 2.93 (t, 2H), 3.10 (m, 1H), 3.25 (m, 1H), 3.45 (m, 2H), 3.63 (m, 1H), 3.80 (m, 2H), 3.95 (m, 1H), 4.15 (m, 2H), 4.20 (m, 2H), 4.42 (m, 1H), 5.43 (dd, 1H), 5.80 (d, 1H), 6.63 (m, 1H), 7.20 (m, 4H), 7.26 (m, 2H).

Alternatively, compound L495 was produced from aldehyde 41b using the similar methods:

EXPERIMENTAL EXAMPLE 1

Experiments for evaluating the antineoplasmic activities at a cellular level

1. EXPERIMENTAL OBJECT

The experiments for evaluating the antineoplasmic activities of the compounds according to the present invention were carried out, and the compounds' antineoplasmic activities in vitro was evaluated by determining the inhibitory activities thereof against the proliferation of MDA-MB-435S human breast cancer cells.

2. EXPERIMENTAL PRINCIPLE

The antineoplasmic activities were determined by using the MTT assay, which is based on the metabolic reduction of 3-(4,5-dimethylthylthiazol-2-yl)-2,5-diphenyl tetrazolium bromide (MTT). The dehydrogenases, which are related to NADP (niacinamide adenine dinucleotide phosphate, coenzyme) and present in mitochondrions of living cells, can reduce the yellow MTT to an insoluble, dark purple formazan. Such dehydrogenase do not exist in dead cells, and thus MTT can not be reduced. After the formazan is dissolved in DMSO, the optical density is determined on an ELISA Reader at the wavelength of 550/690 nm.

3. EXPERIMENTAL PROCEDURE

The adhered MDA-MB-4355 cells in logarithmic growth phase, were digested by 0.05% trypsogen, counted and formulated into a cell suspension with a medium. After counted, the suspension was inoculated on a 96-well plate with 3000 cells and 100 μl medium per well. The inoculated 96-well plate was placed overnight in an incubator at 37 with 5% CO$_2$ to allow the cells to adhere to the wall. On the next day, the administration of the drugs started. Before the administration, into some of the control wells, each was added 20 μl of the MTT solution (5 mg/ml) without removing the medium

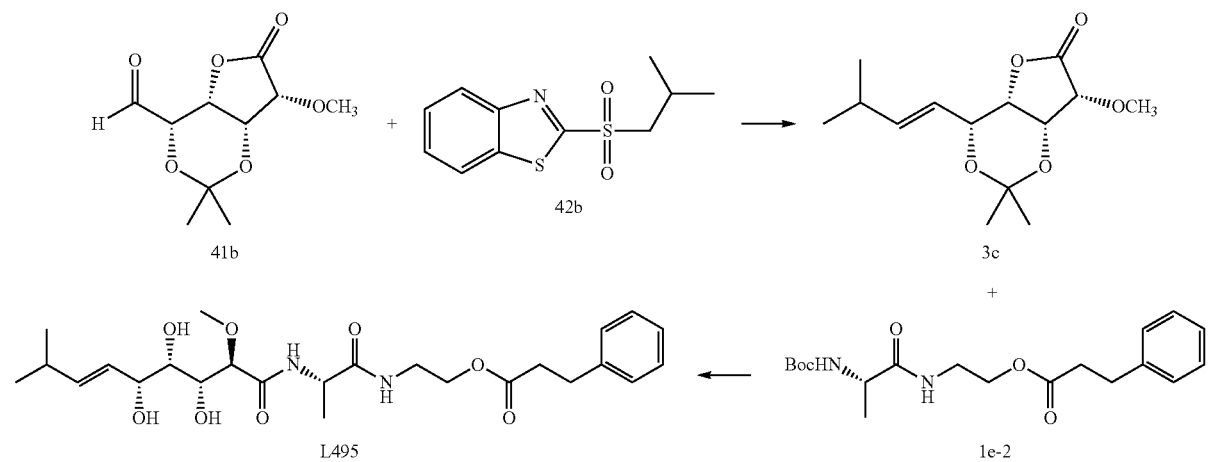

$^1$H NMR (CDCl$_3$, 300 MHz): δ 1.09 (d, 6H), 1.40 (d, 3H), 2.53 (m, 1H), 2.64 (t, 2H), 2.93 (t, 2H), 3.10 (m, 1H), 3.42 (s, 3H), 3.46 (m, 2H), 3.63 (m, 1H), 3.80 (m, 2H), 3.95 (m, 1H), 4.15 (m, 2H), 4.20 (m, 2H), 4.42 (m, 1H), 5.43 (dd, 1H), 5.80 (d, 1H), 6.63 (m, 1H), 7.20 (m, 4H), 7.26 (m, 2H).

therein. After incubated for 3 h, the absorption at A550/690 was recorded as the initial cell concentration. For the drug wells, each was added into 100 μl of medium containing 2 μl of compound solution. For the control wells which use DMSO as background control, each was also added into 100

μl of medium containing 2 μl of DMSO. In addition, each experiment was carried out with adriamycin as the positive control. Subsequently, the 96-well plate was incubated in an incubator at 37 with 5% $CO_2$ for 72 h. each compound was tested in triplicate wells (6 μl of compound solution was put into a sterilized eppendorf centrifuge tube, then 300 μl of medium was added and mixed well, and the mixture was distributed into 3 wells respectively), and at six concentrations which form a gradient. 3 days (72 h) later, 40 μl of MTT solution (5 mg/ml) was put into each well directly (without sucking off the medium therein), and the plate was incubated in the incubator for 3 h and then taken out. The liquid in each well was sucked off, and then 100 μl of DMSO was put into each well to dissolve the crystal completely with slight shake. The absorbance of the solution in each well was determined at 550/690 nm on an ELISA Reader as the cell density after treated with the compound. The growth inhibition of compound against breast cancer cells MDA-MB-435S was represented by the cell survival rate, and $IC_{50}$ was determined from the profile of cell survival rate vs compound concentration. The calculating formula was as follows:

cell survival rate=[(cells+compound)$A_{550/690}$/(cells+compound vector DMSO)$A_{550/690}$]×100%

The experimental results are showed in the following table 6.

TABLE 6

Experimental results of the tests on Antineoplasmic Activity at Cellular Level

| Serial Number of the Sample | Cell Survival Rate $IC_{50}$ (μM) | Serial Number of the Sample | Cell Survival Rate $IC_{50}$ (μM) |
|---|---|---|---|
| L400 | 9.68 | L486e | 2.85 |
| L415 | NT | L388 | NT |
| L558b | 1.90 | L586 | 0.85 |
| L432 | 4.57 | L474b | 0.72 |
| L444i | NT | L452 | 5.25 |
| L372 | 3.53 | L418b | 1.50 |
| L458 | 0.89 | L491 | 5.13 |
| L474 | 8.86 | L376 | 5.44 |
| L500b | 0.14 | L444g | 6.07 |
| L500a | 0.80 | L480 | 2.37 |
| L472-4 | 1.54 | L471 | 4.79 |

TABLE 6-continued

Experimental results of the tests on Antineoplasmic Activity at Cellular Level

| Serial Number of the Sample | Cell Survival Rate $IC_{50}$ (μM) | Serial Number of the Sample | Cell Survival Rate $IC_{50}$ (μM) |
|---|---|---|---|
| L466 | ≈10 | L485 | 3.15 |
| L472 | >2.5 | L643 | 1.56 |
| L432a | 40 | L514c | 2.22 |
| L432b | 21.64 | L528c | 2.91 |
| L458e | 2.19 | L528b | 2.62 |
| L418c | 13.89 | L528a | 3.24 |
| L460 | 3.38 | L472-3 | 0.72 |
| L446a | 7.06 | L446b | 9.56 |
| L502 | 2.55 | L418 | 5.17 |
| L538 | 0.43 | L558a | 0.20 |
| L521 | 25.18 | L486d | 0.28 |
| L508 | 0.096 | L471b | 0.11 |
| L484 | 0.54 | L500c | 1.93 |
| L538 | 0.49 | L498c | 41.60 |
| L541 | 0.70 | L572 | 0.11 |
| L508 | 0.40 | L538b | 0.76 |
| L589 | 0.88 | LAF389 | 0.61 |
| adriamycin | 0.51 | | |

Notes:
1. The activity in table 6 is the in vitro activity of compound against human breast cancer cells MDA-MB-435S;
2. $IC_{50}$ is the concentration of the sample compound that is required for 50% inhibition of the cell growth;
3. NT means untested.

As can be seen from the above results, over 30 compounds have an $IC_{50}$ less than 500 nM, wherein 6 compounds less than 100 nM, and 4 compounds less than 50 nM.

EXPERIMENTAL EXAMPLE 2

Activity assay for some compounds on multiple antitumor models

MDA-MB-435S: human breast cancer cells; HCT116: colon cancer cells; A549: lung adenocarcinoma cells; Hela: uterine cervix cancer cells.

The tests were performed in the same manner as that of experimental example 1, except that for Hela cells, after counted, each well was seeded with 1000 cells and 100 μl of medium on a 96-well plate.

The experimental results are showed in the following table 7.

TABLE 7

Activities of some compounds on multiple antitumor models

| Serial Number of the Sample | $IC_{50}$ (μmol/L) (MDA-MB-435) | $IC_{50}$ (μmol/L) (HCT116) | $IC_{50}$ (μmol/L) (A549) | $IC_{50}$ (μmol/L) (Hela) |
|---|---|---|---|---|
| L486d | 0.284 ± 0.100 | 0.097 ± 0.013 | 0.075 ± 0.014 | 0.165 ± 0.030 |
| L558a | 0.201 ± 0.047 | 0.051 ± 0.005 | 0.098 ± 0.018 | 0.024 ± 0.003 |
| L418 | 5.170 ± 0.941 | 1.505 ± 0.215 | 1.549 ± 0.241 | 0.572 ± 0.171 |
| L458e | 2.833 ± 0.695 | 1.510 ± 0.283 | 0.594 ± 0.069 | 0.822 ± 0.175 |
| L484 | 0.541 ± 0.205 | 0.130 ± 0.015 | 0.219 ± 0.030 | 0.188 ± 0.042 |
| L538 | 0.494 ± 0.139 | 0.098 ± 0.009 | 0.133 ± 0.025 | 0.091 ± 0.019 |
| L508 | 0.398 ± 0.128 | 0.071 ± 0.007 | 0.076 ± 0.008 | 0.158 ± 0.032 |
| L498c | 41.591 ± 11.099 | 17.989 ± 1.857 | 32.211 ± 8.960 | 27.353 ± 7.564 |
| Adriamycin | 0.510 ± 0.124 | 0.110 ± 0.013 | 0.261 ± 0.065 | |

Notes:
1. $IC_{50}$ is the concentration of the sample compound that is required for 50% inhibition of cell growth; The activity in table 7 are the in vitro activity of the compound against human breast cancer cells MDA-MB-435S, colon cancer cells HCT116, lung cancer cells A549 and Helauterine cervix cancer cells.

The results showed that, except for individual compounds, most of the tested compounds have significant growth inhibitory activities in vitro against the above cancer cells, indicating that such compounds have a broad-spectrum antineoplasmic activity in vitro.

EXPERIMENTAL EXAMPLE 3

Antineoplasmic activity assay in vivo.

Experimental object: to evaluate the growth inhibitory effect of L538 against human breast cancer cells MDA-MB-435 transplanted on nude mice.

Test compound: L538, which was diluted with physiologic saline to a desired concentration.

Positive control: mitomycin (MMC), Kyowa Hakko Kirin Co. Ltd., batch No.: 020301, 2 mg/bottle, diluted with physiologic saline before use.

Dosage: among 3 groups, the dosages of L538 were set at 5, 10 and 20 mg/kg as the high, middle and low dosages, respectively, administrating intravenously 3 times a week; while MMC was administrated intravenously at the first day whit a dosage of 5 mg/kg.

Animals: BALB/CA nude mice, male, 40-45 days old, body weight: 18±1 g, provided by Shanghai Institute of Materia Medica, Chinese Academy of Sciences. License No.: Certificate No. 122 of experimental animals, Shanghai. Animal number in each group: 7 in negative control group, and 4 in administration group.

Transplanted tumor: human breast cancer cells MDA-MB-435 transplanted on nude mice, which was formed by inoculating human breast cancer cell line MDA-MB-435 on nude mice subcutaneously. The amount of inoculated cells was $5 \times 10^6$. After the transplanted tumor was formed by inoculation, it was used after passed for 3 generations in nude mice.

Experimental procedure: tumor tissue in productive phase was cut into nubs of about 1.5 mm$^3$. Under sterile conditions, the nubs were inoculated subcutaneously in right axillary fossa of the nude mice. The diameters of the transplanted tumors on nude mice were measured by a vernier caliper. When the tumors grew up to 100-200 mm$^3$, the animals were divided randomly into groups. Mice in experimental groups were administered intravenously every other day. After administered 4 times, the mice showed too strong tail stimulus to be administered intravenously, and thus were administrated peritoneally 5 times. The total administration duration was 3 weeks. For the positive control, MMC, Mice were administered intravenously once at the first day of a week, and the total administration duration was 3 weeks. Mice in control groups were administrated physiologic saline in equivalent amount. The diameter of the tumor and weight of mice were measured twice a week. The equation for calculating the TV (tumor volume) was as follows:

$$TV = 1/2 \times a \times b^2,$$

wherein, a is length and b is width. RTV (relative tumor volume) was calculated based on the measured results, and the equation thereof was as follows:

$$RTV = V_t/V_0$$

wherein, $V_0$ is the tumor volume measured when the mice were grouped (i.e. d0), and Vt is the tumor volume at each measurement. The evaluation index for the antitumor activity was the relative tumor proliferation rate T/C (%).

The calculation equation was as follows:

$$T/C(\%) = (TRTV/CRTV) \times 100,$$

wherein, TRTV is the RTV of therapeutic Group and CRTV is RTV of negative control group.

Evaluation standard for the curative effect: T/C (%)>60% indicates ineffective, while T/C (%)<=60 with a statistic result of p<0.05 represents effective.

Figure 2:
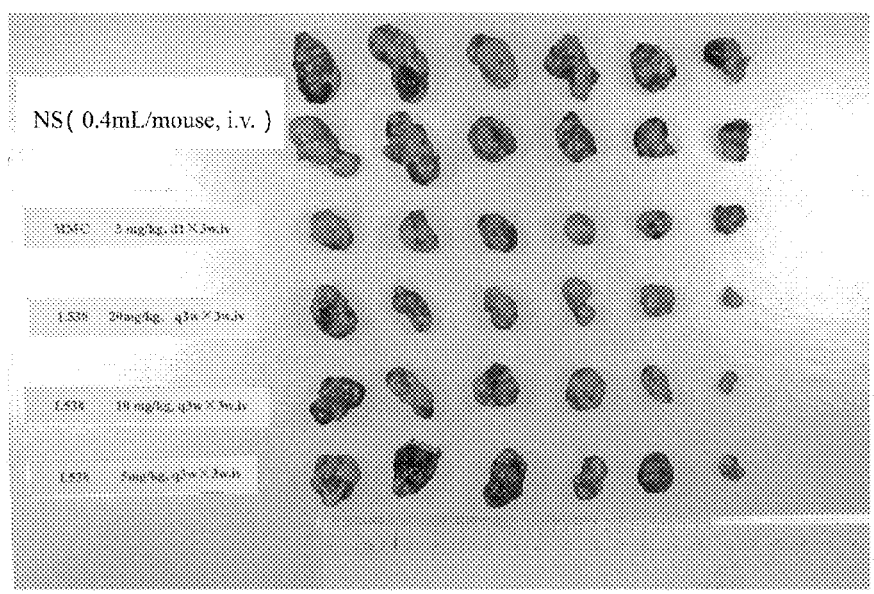
FIG. 2 is a solid photograph of the transplanted tumors illustrating the experimental therapeutic effects of the active compound L538 on the MDA-MB-435 transplanted tumor, which is developed by subcutaneously inoculating human breast cancer MDA-MB-435 cell line on nude mice.

Results: The growth inhibition of L538 against human breast cancer cells MDA-MB-435 transplanted on nude mice was showed in table 8, and FIGS. 1 and 2. The above results demonstrated that among experimental groups (wherein the mice thereof were administered intravenously every other day, and after administered 4 times, the mice showed too strong tail stimulus to be administered intravenously, and thus were administered peritoneally 5 times, and the total administration duration was 3 weeks), the middle and high dosage groups showed marked growth inhibitory activities against human breast cancer cells MDA-MB-435 transplanted on nude mice with T/C of 47.1% and 36.0 respectively. The nude mice in the high dosage group did not have an significant increase in body weight, while the human breast cancer cells MDA-MB-435 transplanted on nude mice did not be depressed obviously in the low dosage group, and none of the experimental groups had dead nude mice. MMC (which was administered intravenously on the first day with the dosage of 5 mg/kg) as the positive control had significantly growth inhibitory activities against human breast cancer cells MDA-MB-435 transplanted on nude mice with a T/C of 44.3%.

TABLE 8 the experimental therapeutic effects of L538 against human breast cancer cells MDA-MB-435 transplanted on nude mice

| Group | Dosage/Administration | Mode | Quantity of Animals | | Body Weight(g) | | TV (mm$^3$) | | RTV | T/C (%) | P value |
|---|---|---|---|---|---|---|---|---|---|---|---|
| | | | Initial | Ultimate | Initial | Ultimate | d0 | d21 | | | |
| NS | 0.2 ml/one mouse | i.v. | 12 | 12 | 18.3 | 22.9 | 133 ± 64 | 1730 ± 501 | 15 ± 6.3 | | |
| MMC | 5 mg/kg, d1 | i.v. | 6 | 6 | 17.8 | 21.7 | 132 ± 52 | 844 ± 308 | 6.6 ± 1.6 | 44.3 | <0.05 |
| L538 | 20 mg/kg, q3w × 3w | i.v. | 6 | 6 | 18.5 | 19.7 | 135 ± 37 | 735 ± 501 | 5.3 ± 3.1 | 36.0 | <0.05 |
| L538 | 10 mg/kg, q3w × 3w | i.v. | 6 | 6 | 17.7 | 21.7 | 133 ± 49 | 951 ± 619 | 6.9 ± 3.6 | 47.1 | <0.05 |
| L538 | 5 mg/kg, q3w × 3w | i.v. | 6 | 6 | 19.3 | 23.5 | 131 ± 59 | 1144 ± 353 | 9.6 ± 3.5 | 64.7 | >0.05 |

Notes:
The mice were administered intravenously 4 times, then administered peritoneally 5 times due to the strong tail stimulus.

Conclusions: L538 can significantly depress the growth of human breast cancer cells MDA-MB-435 transplanted on nude mice, and shows a good dose-efficiency relationship.

EXPERIMENTAL EXAMPLE 4

Antineoplasmic activity assay of the Bengamides according to the present invention.

4.1 The Cytotoxicities of the Bengamides According to the Present Invention:

Experimental method: The antineoplasmic activities in vitro of the compounds were determined by SRB assay. The detailed procedure was as follows. The cells in the logarithmic growth phase were inoculated on a 96-well microculture plate with a suitable density (100 µl/well), and allowed to attach overnight, followed by addition of the compound at different concentrations to be treated for 72 h. For each concentration, the test was carried out in triplicate wells, and included control wells containing the aqueous medium of normal saline and a blank well containing all medium without cells for zeroing. After cultured overnight, the cells were treated with the compound at different concentrations for 72 h. After the treatment, the culture medium was removed, and the cells were fixed with 10% (wt/vol) trichloroacetic acid (100 µL/well) at 4° C. for 1 h. The cells were then washed with distilled water for 5 times, and died at room temperature, followed by addition of a SRB solution (4 mg/mL, dissolved in 1% glacial acetic acid) at 100 µL/well. The cells were incubated and stained at room temperature for 15 min, then washed with 1% glacial acetic acid for 5 times to remove the uncombined SRB, and died at room temperature. 100 µL of 10 mM Tris solution was added in each well, and the Optical Density (OD) were measured at a wavelength of 560 nm on a VERSMax ELISA Reader (Molecule Devices). The growth inhibition of the compound against tumor cells was calculated according to the following equation: Growth inhibition (%)=($OD_{control}$−$OD_{treated}$)/$OD_{control}$×100%.

$IC_{50}$ (the concentration of the sample compound that is required for 50% inhibition of cell growth) was calculated by using the Logit method based on the measurement, and each test was repeated for 3 times to calculate the mean value and standard deviation.

Results: The above results showed that except for individual cell lines, all of the three compounds evaluated had marked antineoplasmic activities in vitro for most of tumor cells (see Table 9), especially for lung cancer cells and liver cancer cells, and it was deduced that such compounds had a certain cytotoxicity.

The invention claimed is:

1. An α-amino-N-substituted amide compound having a structure represented by following formula, or a pharmaceutically acceptable salt thereof:

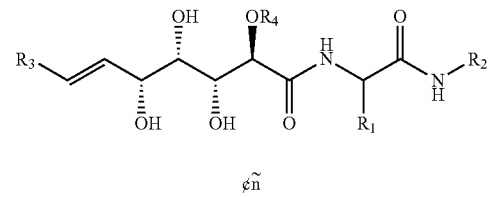

wherein, $R_1$ is H or a substituted/unsubstituted C1-C10 alkyl, wherein the substituents of the substituted C1-C10 alkyl are selected from the group consisting of C1-C10 alkoxyl, C1-C10 alkylthio, hydroxyl, aminocarbonyl, C1-C10 alkoxylcarbonyl, C1-C10 alkoxylcarbonylamino, aryl, fused heteroaryl or (1-phenyl C1-4 alkoxylenemethylene)imidazolyl;

$R_2$ is one selected from the group consisting of vinyl C1-C10 alkylene; hydroxyl C1-C10 alkylene; C3-C8 cycloalkyl aminocarbonyl C1-C10 alkylene; C3-C8 cycloalkoxyl carbonyl C1-C10 alkylene; C1-C10 alkoxyl carbonyl C1-C10 alkylene; C1-C10 alkoxyl C1-C10 alkylene; C3-C8 cycloalkoxyl C1-C10 alkylene; phenyl C1-C4 alkoxylene C1-C10 alkylene; C3-C8 saturated or unsaturated cycloalkyl carbonyloxy C1-C10 alkylene; C3-C8 cycloalkyl carbonyl amino C1-C4 alkylene; C3-C8 cycloalkyl C1-C4 alkylene carbonyloxy C1-C10 alkylene; adamantyl carbonyloxy C1-C10 alkylene; phenyl carbonyloxy C1-C10 alkylene; furyl carbonyloxy C1-C10 alkylene; phenyl C1-C4 alkylene carbonyloxy C1-C10 alkylene; C1-C15 alkyl carbonyloxy C1-C10 alkylene; acetenyl C1-C10 alkylene carbonyloxy C1-C10 alkylene; C1-C15 alkoxyl

TABLE 9

The in vitro antineoplasmic activities of the present compounds

| | | $IC_{50}$ (µM) (mean ± SD) | | | |
|---|---|---|---|---|---|
| Tissue resource | Cell line | L508 | L538 | L558a | LAF389 |
| Lung Cancer | A549 | 0.03 ± 0.01 | 0.02 ± 0.004 | 0.08 ± 0.02 | 0.05 ± 0.01 |
| Gastric Cancer | SGC-7901 | 2.21 ± 0.67 | 3.92 ± 1.78 | 1.97 ± 0.86 | 4.96 ± 0.40 |
| Colon Cancer | HCT-116 | 0.35 ± 0.11 | 0.24 ± 0.10 | 0.58 ± 0.25 | 0.63 ± 0.18 |
| Ovarian Cancer | HO-8910 | >20 | >20 | >20 | >20 |
| Prostatic Cancer | DU145 | 0.29 ± 0.06 | 0.14 ± 0.04 | 0.14 ± 0.01 | 0.42 ± 0.21 |
| Liver Cancer | BEL-7402 | 0.33 ± 0.21 | 0.37 ± 0.27 | 0.28 ± 0.01 | 0.56 ± 0.40 |
| | SMMC-7721 | 0.65 ± 0.26 | 0.58 ± 0.04 | 0.41 ± 0.15 | 1.25 ± 0.76 |
| | Zip177 | 0.40 ± 0.21 | 0.37 ± 0.06 | 0.26 ± 0.05 | 2.79 ± 0.15 |
| | HepG2 | 0.56 ± 0.08 | 0.45 ± 0.07 | 1.11 ± 0.49 | 0.21 ± 0.09 |
| | 7404 | >20 | >20 | >20 | >20 |
| Breast Cancer | MDA-MB-435 | 0.08 ± 0.01 | 0.09 ± 0.01 | 0.14 ± 0.13 | 0.29 ± 0.02 |
| Pancreatic Cancer | HPAF-II | 1.57 ± 0.35 | 0.65 ± 0.21 | 2.01 ± 1.06 | 3.23 ± 2.13 |
| Others | HMEC | 0.21 ± 0.02 | 0.17 ± 0.06 | 0.25 ± 0.14 | 0.83 ± 0.45 | carbonyloxy C1-C10 alkylene; C3-C8 cycloalkoxyl carbonyloxy C1-C10 alkylene; phenyl C1-C10 alkoxylene carbonyloxy C1-C10 alkylene; azido C1-C15 alkylene carbonyloxy C1-C10 alkylene; alkylidyne of formula

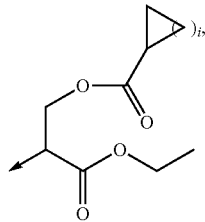

wherein i is an integer of 1 to 6; spirolactone alkylene of formula

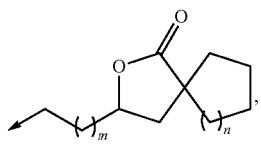

wherein m is an integer of 0 to 5, and n is an integer of 0 to 4; and lactone methylene of formula

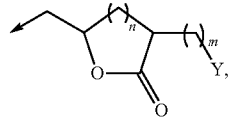

wherein m is an integer of 0 to 5, n is an integer of 0 to 4, and Y is phenyl or a C1-C10 alkyl;
$R_3$ is a C1-C10 alkyl;
$R_4$ is a C1-C5 alkyl;
in the case of when the carbon atom connected to $R_1$ is a chiral carbon atom and/or $R_2$ contains a chiral carbon atom, the said α-amino-N-substituted amide compound may be a optically pure stereoisomer or a mixture thereof.

2. The α-amino-N-substituted amide compound or the pharmaceutically acceptable salt thereof according to claim 1, wherein $R_3$ is a C1-C4 alkyl, and $R_4$ is a C1-C4 alkyl.

3. The α-amino-N-substituted amide compound or the pharmaceutically acceptable salt thereof according to claim 2, wherein $R_3$ is tert-butyl or isopropyl, and $R_4$ is methyl or isopropyl.

4. The α-amino-N-substituted amide compound or the pharmaceutically acceptable salt thereof according to claim 1, wherein $R_1$ is a substituted or unsubstituted C1-C4 alkyl, wherein, the subsituents of the substituted C1-C4 alkyl are selected from C1-C4 alkoxyl, C1-C4 alkylthio, hydroxyl, aminocarbonyl, C1-C4 alkoxylcarbonyl, C1-C4 alkoxyl carbonyl amino, phenyl, indyl, benzofuryl, benzothienyl, N-methylindyl or 1-benzyloxy-methylene imidazolyl.

5. The α-amino-N-substituted amide compound or the pharmaceutically acceptable salt thereof according to claim 4, wherein $R_1$ is methyl, isopropyl, isobutyl, 2-methylpropyl or n-butyl, or is a C1-C4 alkyl substituted by tert-butoxy, methylthio group, 4-(1-benzyloxy-methylene)imidazolyl, hydroxyl, tert-butoxy carbonyl, aminocarbonyl, 3-indyl, phenyl or tert-butoxy carbonyl amino.

6. The α-amino-N-substituted amide compound or the pharmaceutically acceptable salt thereof according to claim 1, wherein $R_2$ is one selected from the group consisting of vinyl C1-C4 alkylene; hydroxyl C1-C4 alkylene; C3-C6 cycloalkyl amino carbonyl C1-C4 alkylene; C3-C6 cycloalkoxyl carbonyl C1-C4 alkylene; C1-C4 alkoxyl carbonyl C1-C4 alkylene; C1-C4 alkoxyl C1-C4 alkylene; C3-C6 cycloalkoxyl C1-C4 alkylene; phenyl C1-C4 alkoxylene C1-C4 alkylene; C3-C6 saturated or unsaturated cycloalkyl carbonyloxy C1-C4 alkylene; cyclohexyl carbonyl amino C1-C4 alkylene; C3-C6 cycloalkyl C1-C4 alkylene carbonyloxy C1-C4 alkylene; adamantyl carbonyloxy C1-C4 alkylene; phenyl carbonyloxy C1-C4 alkylene; furyl carbonyloxy C1-C4 alkylene; phenyl C1-C4 alkylene carbonyloxy C1-C4 alkylene; C1-C15 alkyl carbonyloxy C1-C4 alkylene; acetenyl C1-C10 alkylene carbonyloxy C1-C4 alkylene; C1-C15 alkoxyl carbonyloxy C1-C4 alkylene; C3-C8 cycloalkoxyl carbonyloxy C1-C4 alkylene; phenyl C1-C6 alkoxylene carbonyloxy C1-C4 alkylene; azido C1-C15 alkylene carbonyloxy C1-C4 alkylene; alkylidyne of formula

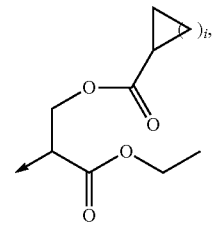

wherein, i is an integer of 1 to 4; spirolactone alkylene of formula

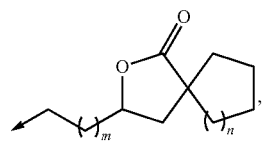

wherein, m is an integer of 0 to 3, and n is an integer of 0 to 2; and lactone methylene of formula

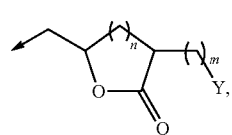

wherein m is an integer of 0 to 3, n is 0 to 2, and Y is phenyl or a C1-C10 alkyl.

7. The α-amino-N-substituted amide compound or the pharmaceutically acceptable salt thereof according to claim 4, wherein $R_3$ is tert-butyl or isopropyl;

R4 is methyl or isopropyl; and the combination of R1 and R2 may be as follow, in the case of when R1 is a substituted or unsubstituted C1-C4 alkyl, wherein, the substituent of the substituted C1-C4 alkyl is selected from the group consisting of C1-C4 alkoxyl, C1-C4 alkylthio, hydroxyl, amino carbonyl, C1-C4 alkoxyl carbonyl and 1-benzyloxymethylene imidazolyl, R2 is a vinyl C1-C4 alkylene; or in the case of when R1 is a substituted or unsubstituted C1-C4 alkyl, wherein, the substituent of the substituted C1-C4 alkyl is selected from the group consisting of 3-indyl and phenyl, R2 is a hydroxyl C1-C4 alkylene; or in the case of when R1 is a substituted or unsubstituted C1-C4 alkyl, wherein, the substituent of the substituted C1-C4 alkyl is a C1-C4 alkoxyl carbonyl amino, R2 is one selected from the group consisting of C3-C6 cycloalkyl amino carbonyl C1-C4 alkylene; C3-C6 cycloalkoxyl carbonyl C1-C4 alkylene; C1-C4 alkoxyl carbonyl C1-C4 alkylene; C1-C4 alkoxyl C1-C4 alkylene; C3-C6 cycloalkoxyl C1-C4 alkylene; phenyl C1-C4 alkoxylene C1-C4 alkylene; C3-C6 saturated or unsaturated cycloalkyl carbonyloxy C1-C4 alkylene; cyclohexyl carbonyl amino C1-C4 alkylene; C3-C6 cycloalkyl C1-C4 alkylene carbonyloxy C1-C4 alkylene; adamantyl carbonyloxy C1-C4 alkylene; phenyl carbonyloxy C1-C4 alkylene; furyl carbonyloxy C1-C4 alkylene; phenyl C1-C4 alkylene carbonyloxy C1-C4 alkylene; C1-C15 alkyl carbonyloxy C1-C4 alkylene; acetenyl C1-C10 alkylene carbonyloxy C1-C4 alkylene; C1-C15 alkoxyl carbonyloxy C1-C4 alkylene; C3-C8 cycloalkoxyl carbonyloxy C1-C4 alkylene; phenyl C1-C6 alkoxylene carbonyloxy C1-C4 alkylene; azido C1-C15 alkylene carbonyloxy C1-C4 alkylene; alkylidyne of formula

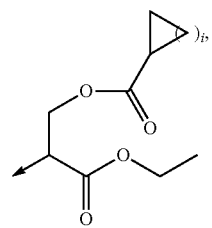

wherein, i is 3 or 4; spirolactone alkylene of formula

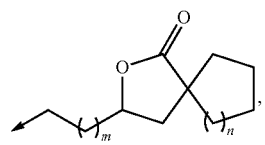

wherein, m is an integer of 0 to 3, and n is an integer of 0 to 2; and lactone methylene of formula

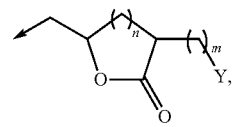

wherein, m is an integer of 0 to 3, n is an integer of 0 to 2, and Y is phenyl or a C1-C10 alkyl.

8. The α-amino-N-substituted amide compound or the pharmaceutically acceptable salt thereof according to claim 7, wherein the α-amino-N-substituted amide compound is one selected from the group consisting of:

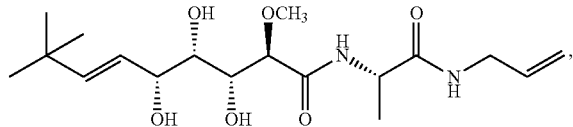

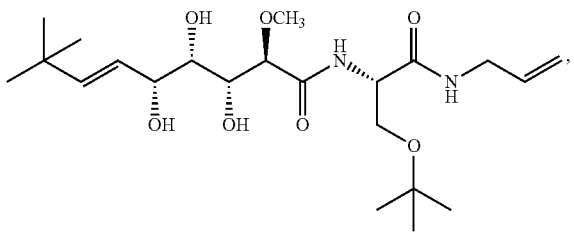

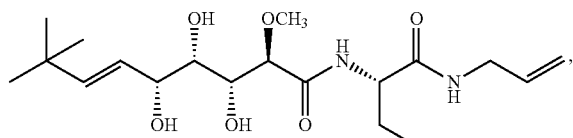

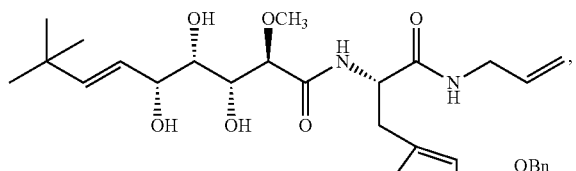

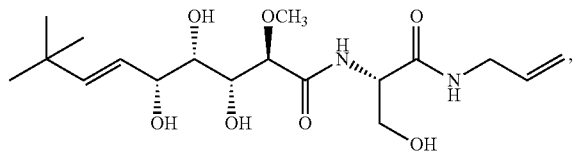

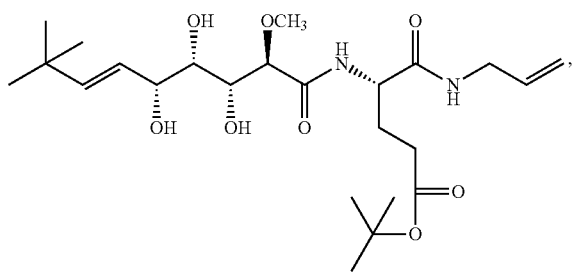

-continued
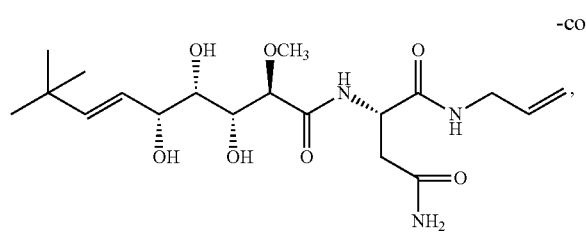
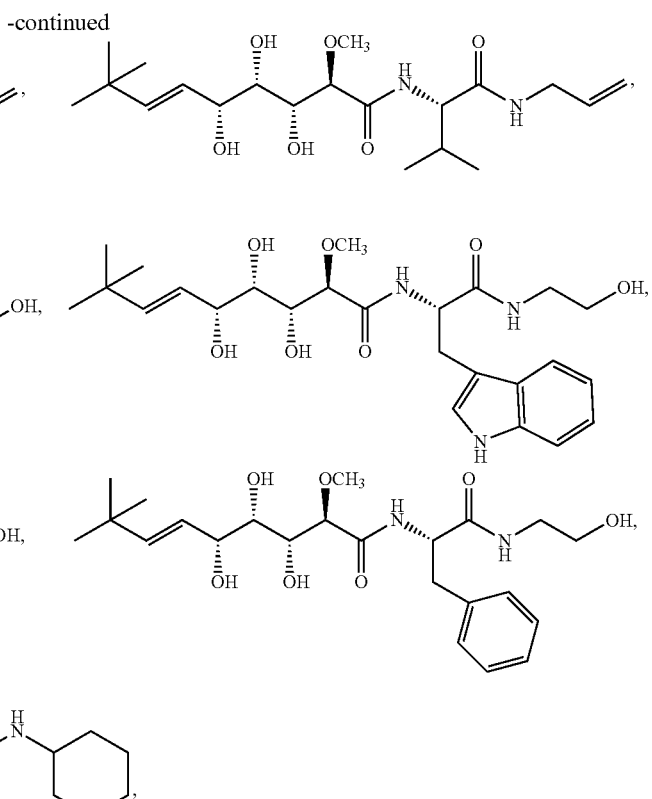
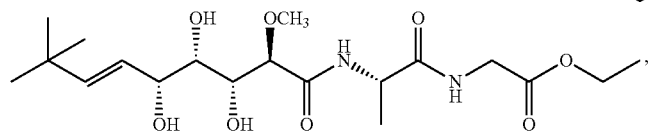
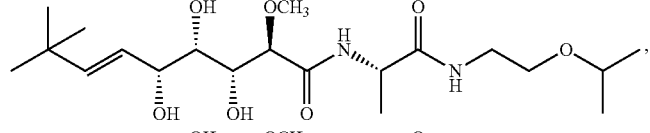
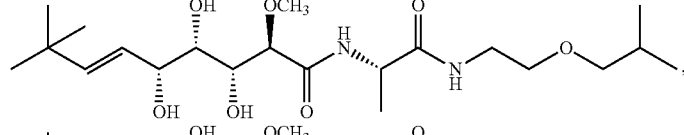
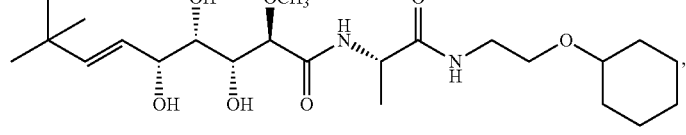
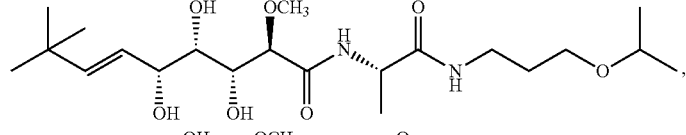
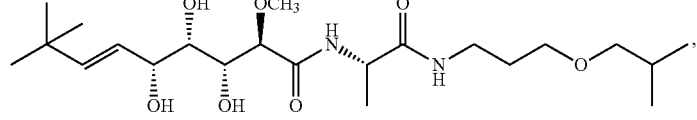

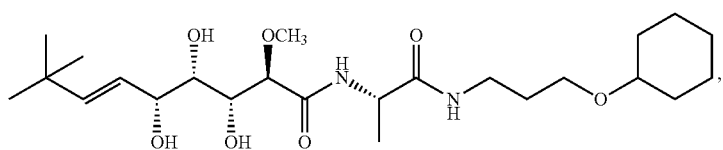
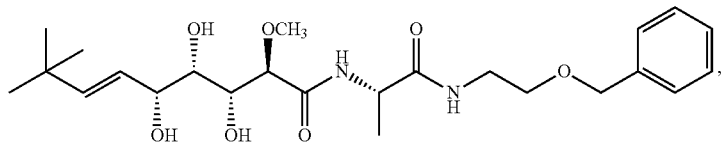
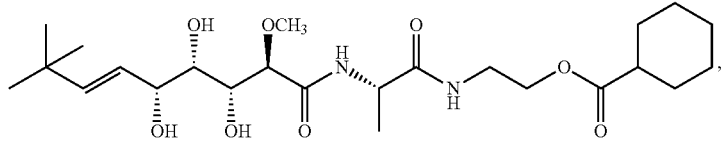
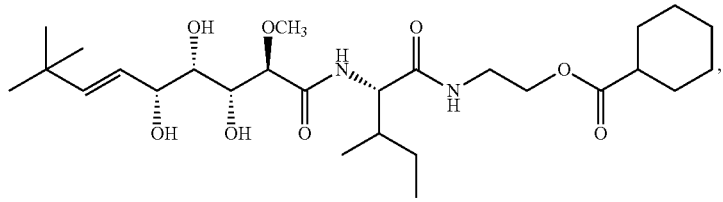
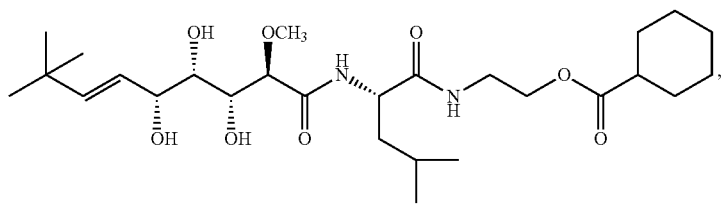
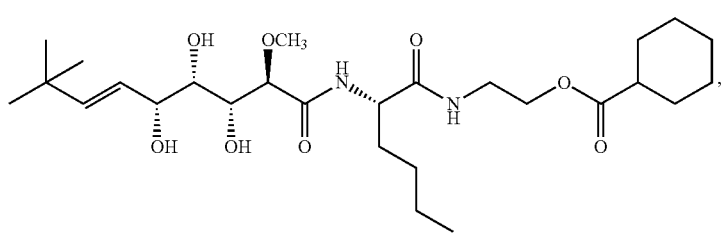
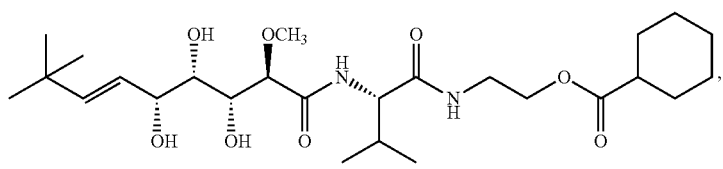
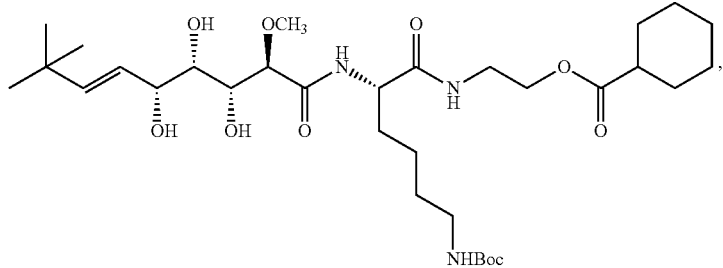
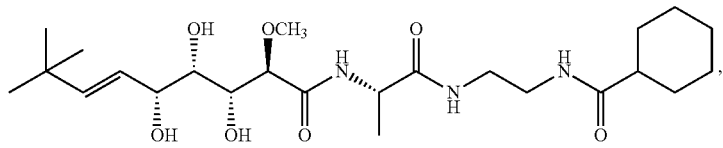

-continued
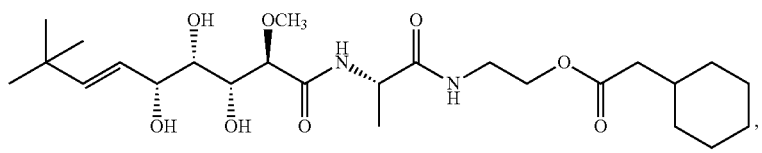
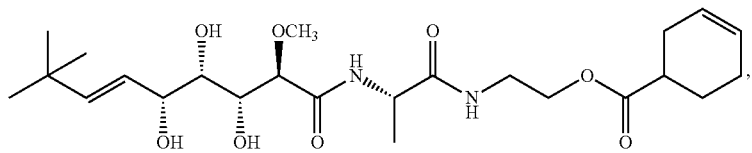
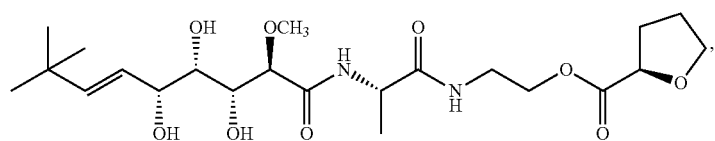
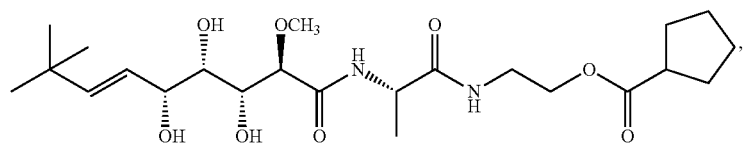
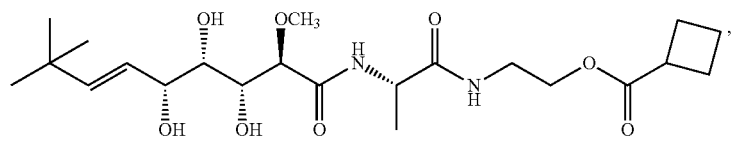
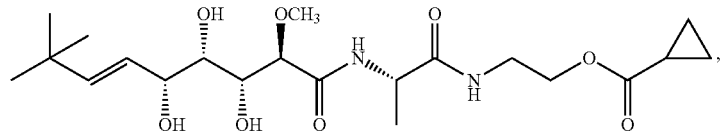
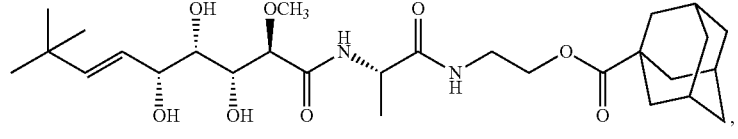
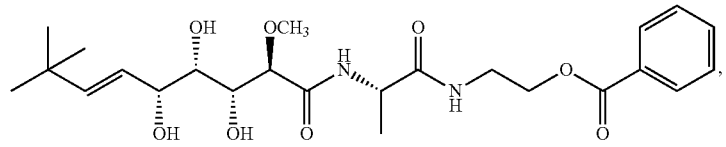
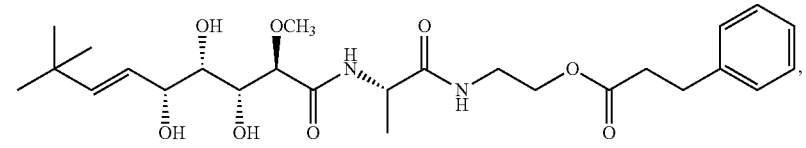
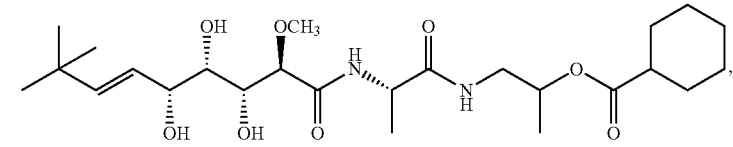

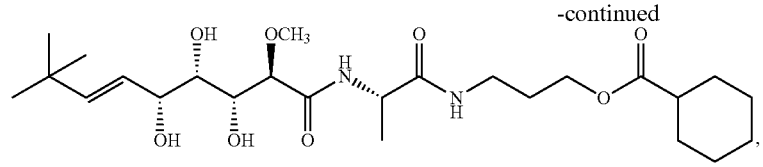
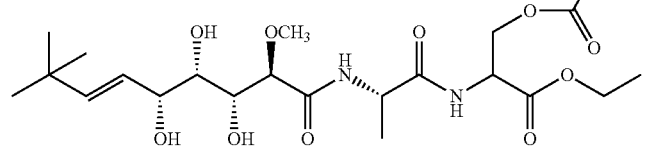
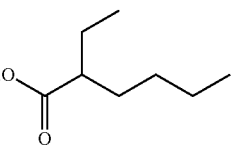
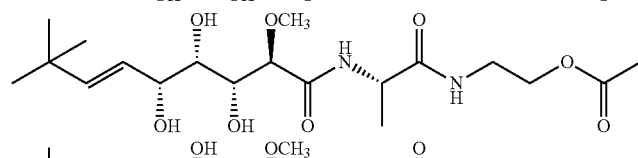
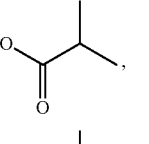
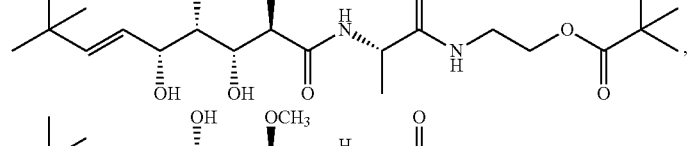
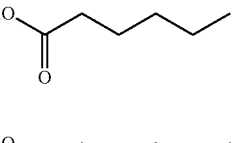
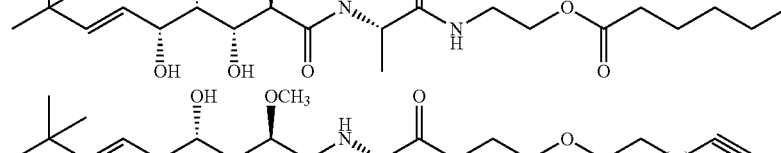
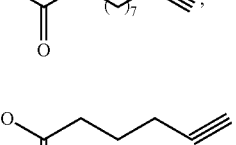
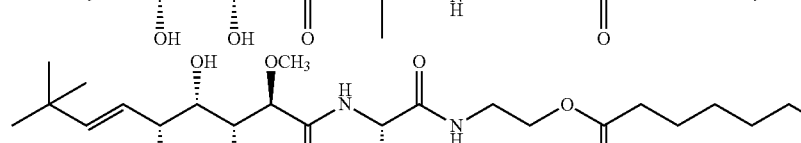
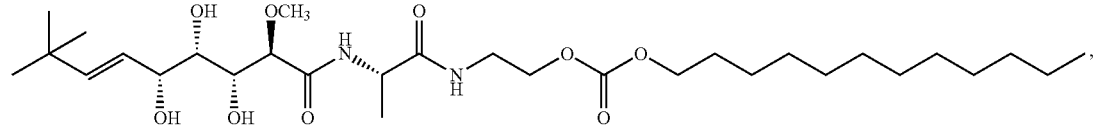

-continued

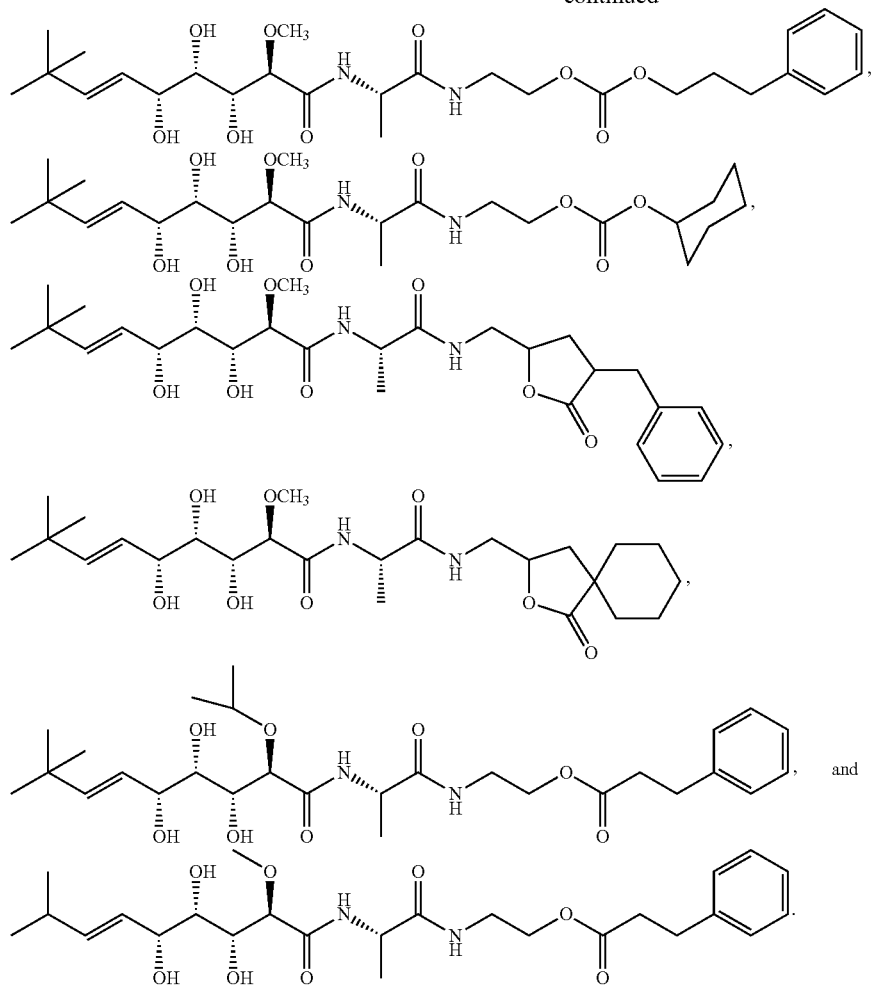

9. The α-amino-N-substituted amide compound, or the pharmaceutically acceptable salt thereof according to claim 1, wherein the pharmaceutically acceptable salt is a salt formed by the α-amino-N-substituted amide compound with hydrochloric acid, sulphuric acid, phosphoric acid, methanesulfonic acid, citric acid, fumaric acid, maleic acid, benzoic acid, benzenesulfonic acid, succinic acid, tartaric acid, lactic acid or acetic acid.

10. A pharmaceutical anti-tumor and/or anti-cancer composition, comprising a therapeutically effective amount of one or more of the α-amino-N-substituted amide compounds or the pharmaceutically acceptable salts thereof according to claim 1 as the active component(s).

11. The pharmaceutical composition according to claim 10, wherein the composition further comprises the conventional pharmaceutical adjuvants.

12. A method of treating cancer comprising administering to a subject in need thereof an effective amount of a compound or the pharmaceutically acceptable salt thereof according to claim 1.

13. The method according to claim 12, wherein the cancer is gastric cancer, ovarian cancer, prostatic cancer, liver cancer, breast cancer, colon cancer, lung cancer or uterine cervix cancer.

* * * * *